(12) United States Patent
Hand et al.

(10) Patent No.: US 6,282,736 B1
(45) Date of Patent: Sep. 4, 2001

(54) PRONING BED

(75) Inventors: Barry D. Hand, Mt. Pleasant; Dana H. Delk, North Charleston; Jack J. Brooks, Folly Beach; Steven J. Doehler, Charleston, all of SC (US)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 09/499,200

(22) Filed: Feb. 7, 2000

Related U.S. Application Data

(63) Continuation of application No. PCT/US98/16497, filed on Aug. 7, 1998, now abandoned.
(60) Provisional application No. 60/090,212, filed on Jun. 22, 1998, and provisional application No. 60/055,043, filed on Aug. 8, 1997.

(51) Int. Cl.[7] ........................................................ A61G 13/04
(52) U.S. Cl. ........................................ 5/608; 5/607; 5/600
(58) Field of Search ..................................... 5/600, 601, 607, 5/608, 609, 610, 611, 629

(56) References Cited

U.S. PATENT DOCUMENTS

| | | |
|---|---|---|
| 1,573,571 | 2/1926 | Pohl . |
| 1,667,982 | 5/1928 | Pearson ................................... 5/608 |
| 1,799,692 | 4/1931 | Knott . |
| 2,076,675 | 4/1937 | Sharp . |
| 2,239,821 | 4/1941 | Knox ....................................... 5/607 |
| 2,311,542 | 2/1943 | Holme . |
| 2,499,101 | 2/1950 | Kluglein . |
| 2,607,103 | 8/1952 | Davidson . |
| 2,613,371 | 10/1952 | Keyes, Jr. . |
| 2,639,206 | 5/1953 | Butler . |
| 2,667,169 | 1/1954 | Kambourakis . |
| 2,673,987 | 4/1954 | Upshaw et al. . |
| 2,880,720 | 4/1959 | Houghtaling . |
| 2,902,701 | 9/1959 | Driskill . |
| 3,049,726 | 8/1962 | Getz . |
| 3,110,912 | 11/1963 | Propst . |
| 3,200,416 | 8/1965 | Warrick . |
| 3,226,734 | 1/1966 | Coventon ................................ 5/607 |
| 3,238,539 | 3/1966 | Koch . |
| 3,286,707 | 11/1966 | Shafer . |
| 3,302,218 | 2/1967 | Stryker ................................... 5/607 |
| 3,344,445 | 10/1967 | Crawford . |
| 3,388,700 | 6/1968 | Mountz . |
| 3,434,165 * | 3/1969 | Keane ..................................... 5/608 |
| 3,451,070 | 6/1969 | Danielson . |
| 3,499,529 | 3/1970 | Katzfey et al. . |
| 3,584,321 | 6/1971 | Buchanan . |
| 3,653,079 | 4/1972 | Bourgraf et al. . |
| 3,658,052 | 4/1972 | Alter . |
| 3,737,924 | 6/1973 | Davis . |
| 3,739,406 | 6/1973 | Koetter . |
| 3,748,666 | 7/1973 | Seng . |
| 3,752,153 | 8/1973 | Copeland . |

(List continued on next page.)

Primary Examiner—Lynne H. Browne
Assistant Examiner—Robert G. Santos
(74) Attorney, Agent, or Firm—Bose McKinney & Evans LLP

(57) ABSTRACT

A bed (10) includes a base (12) having a first end and a second end, and a support assembly (22) coupled to of the base (12) adjacent the first end. The support assembly (22) includes a rotatable drive mechanism (55). The bed (10) also includes a patient support assembly (26) having a support surface (50) for supporting a patient. The patient support assembly (26) has a proximal end (24) and a distal end (25) spaced apart from the proximal end (24) to define a longitudinal axis (38). The proximal end (24) of the patient support assembly (26) is coupled to the drive mechanism (55) of the support assembly (22) so that the distal end (25) of the patient support assembly (26) is cantilevered from the support assembly (22). The drive mechanism (55) is configured to rotate the cantilevered patient support assembly (26) about its longitudinal axis (38).

46 Claims, 13 Drawing Sheets

U.S. PATENT DOCUMENTS

| | | |
|---|---|---|
| 3,765,406 | 10/1973 | Toole et al. . |
| 3,783,863 | 1/1974 | Kliever . |
| 3,814,414 | 6/1974 | Chapa . |
| 3,820,176 | 6/1974 | Feiertag . |
| 3,827,089 * | 8/1974 | Grow ........................................ 5/607 |
| 3,828,377 | 8/1974 | Eary, Sr. . |
| 3,832,742 | 9/1974 | Stryker . |
| 3,851,644 | 12/1974 | Slagle . |
| 3,874,010 | 4/1975 | Geary . |
| 3,884,225 | 5/1975 | Witter . |
| 3,902,204 | 9/1975 | Lee . |
| 3,905,591 | 9/1975 | Schorr et al. . |
| 3,940,808 | 3/1976 | Petrini . |
| 3,941,365 | 3/1976 | Frymoyer . |
| 4,080,673 | 3/1978 | Weisler . |
| 4,084,274 | 4/1978 | Willis et al. . |
| 4,109,329 | 8/1978 | Tupper . |
| 4,152,795 | 5/1979 | Rodosta et al. . |
| 4,156,815 | 5/1979 | Hogan . |
| 4,175,550 * | 11/1979 | Leininger et al. ........................ 601/5 |
| 4,183,110 | 1/1980 | Kidd et al. . |
| 4,244,358 | 1/1981 | Pyers ..................................... 606/242 |
| 4,274,167 | 6/1981 | Immel . |
| 4,277,857 | 7/1981 | Svehaug . |
| 4,356,577 | 11/1982 | Taylor et al. ............................. 5/608 |
| 4,384,378 | 5/1983 | Getz et al. . |
| 4,395,786 | 8/1983 | Casey et al. . |
| 4,432,353 | 2/1984 | Vrzalik . |
| 4,490,867 | 1/1985 | Gabrielsson . |
| 4,572,493 * | 2/1986 | Hubert ...................................... 5/608 |
| 4,578,833 | 4/1986 | Vrzalik ..................................... 5/607 |
| 4,584,989 | 4/1986 | Stith . |
| 4,586,492 | 5/1986 | Manahan . |
| 4,619,270 | 10/1986 | Margolis et al. .................... 600/534 |
| 4,655,206 | 4/1987 | Moody . |
| 4,658,450 | 4/1987 | Thompson . |
| 4,763,643 | 8/1988 | Vrzalik . |
| 4,769,584 | 9/1988 | Irigoyen et al. . |
| 4,827,541 | 5/1989 | Vollman et al. . |
| 4,841,585 * | 6/1989 | Masuzawa .............................. 5/610 |
| 4,852,193 | 8/1989 | Alsip et al. . |
| 4,856,128 | 8/1989 | Alsip et al. . |
| 4,866,796 | 9/1989 | Robinson et al. . |
| 4,868,937 | 9/1989 | Connolly ................................. 5/608 |
| 4,872,657 | 10/1989 | Lussi . |
| 4,912,754 | 3/1990 | Van Steenburg .................... 378/209 |
| 4,920,589 | 5/1990 | LaVelle et al. . |
| 4,924,537 | 5/1990 | Alsip et al. . |
| 4,939,801 | 7/1990 | Schaal et al. . |
| 4,941,221 | 7/1990 | Kanzler . |
| 4,944,054 | 7/1990 | Bossert . |
| 4,947,496 | 8/1990 | Connolly . |
| 4,958,817 | 9/1990 | Heller et al. . |
| 4,960,271 | 10/1990 | Sebring ................................... 5/608 |
| 4,987,622 | 1/1991 | Shockey . |
| 5,005,233 | 4/1991 | Toivio et al. . |
| 5,018,712 | 5/1991 | Schaefer . |
| 5,020,170 | 6/1991 | Ruf . |
| 5,023,968 | 6/1991 | Diehl et al. . |
| 5,048,071 | 9/1991 | Van Steenburg . |
| 5,060,324 | 10/1991 | Marinberg et al. . |
| 5,088,706 | 2/1992 | Jackson . |
| 5,092,007 | 3/1992 | Hasty . |
| 5,103,511 | 4/1992 | Sequin . |
| 5,131,103 | 7/1992 | Thomas et al. . |
| 5,131,105 | 7/1992 | Harrawood et al. .................... 5/607 |
| 5,131,106 | 7/1992 | Jackson . |
| 5,148,815 | 9/1992 | Britton . |
| 5,152,024 | 10/1992 | Chrones et al. . |
| 5,181,288 | 1/1993 | Heaton et al. . |
| 5,208,928 | 5/1993 | Kuck et al. . |
| 5,230,112 * | 7/1993 | Harrawood et al. .................... 5/607 |
| 5,274,862 | 1/1994 | Palmer, Jr. et al. . |
| 5,299,334 | 4/1994 | Gonzalez . |
| 5,319,817 | 6/1994 | Hay et al. . |
| 5,334,186 | 8/1994 | Alexander . |
| 5,404,603 | 4/1995 | Fukai et al. . |
| 5,412,823 | 5/1995 | Sitta . |
| 5,418,990 | 5/1995 | Risasen ................................... 5/608 |
| 5,427,338 | 6/1995 | Garrett et al. . |
| 5,502,853 | 4/1996 | Singleton et al. . |
| 5,515,561 | 5/1996 | Suggitt et al. . |
| 5,515,869 | 5/1996 | Powell et al. . |
| 5,621,932 | 4/1997 | Strachan . |
| 5,664,270 | 9/1997 | Bell et al. . |
| 5,699,568 | 12/1997 | Couldridge . |
| 6,065,165 | 5/2000 | Delk et al. . |
| 6,108,838 | 8/2000 | Connolly et al. . |
| 6,112,349 | 9/2000 | Connolly . |

FOREIGN PATENT DOCUMENTS

| | | |
|---|---|---|
| 0 569 308 A1 | 5/1993 | (EP) . |
| 2034679 | 12/1970 | (FR) . |
| 2 247 194 | 5/1975 | (FR) . |
| 2 549 366 | 1/1985 | (FR) . |
| 2 585 240 | 1/1987 | (FR) . |
| 77886 | 11/1975 | (TW) . |
| WO 93/05745 | 9/1992 | (WO) . |

* cited by examiner

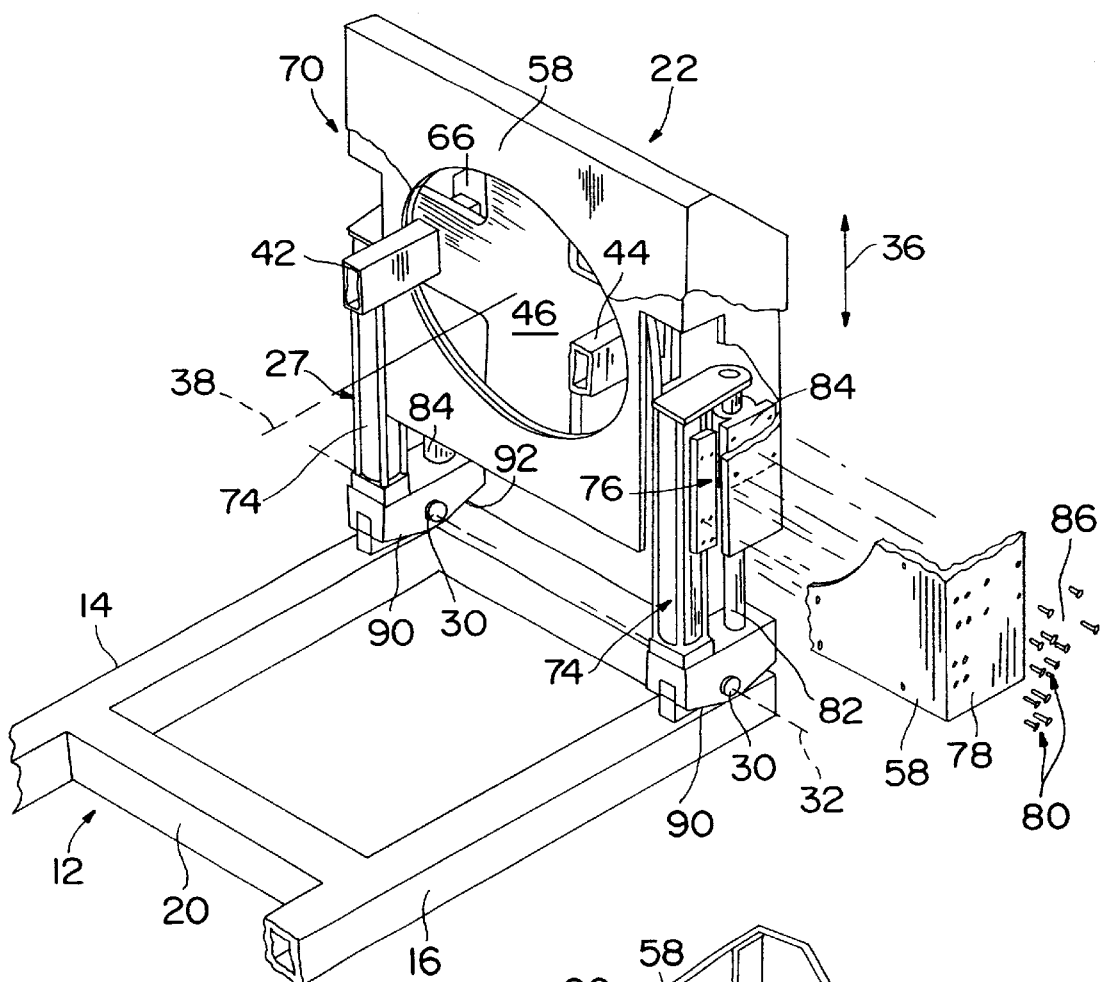
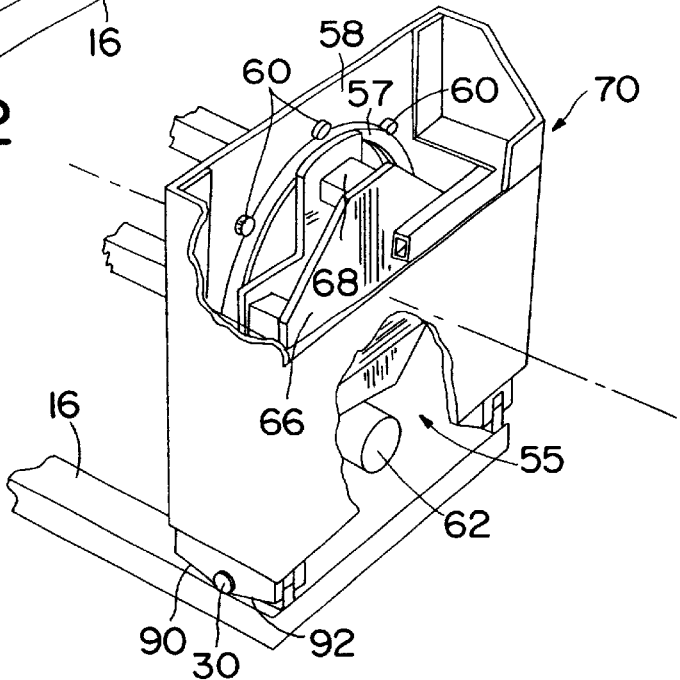
FIG. 2
FIG. 3

PRONING BED

This application is a continuation of International Application PCT/US98/16497, with an international filing date of Aug. 7, 1998, now abandoned.

This application claims benefit of Provisional Application No. 60/055,043 and 60/090,212 filed Aug. 8, 1997 and Jul. 22, 1998, respectively.

BACKGROUND AND SUMMARY OF THE INVENTION

The present invention relates to a hospital bed. More particularly, the present invention relates to a proning bed which permits rotation of a patient supported on a patient support surface of the bed.

A frame of the bed is operated to rotate the patient a fill 360° about a longitudinal axis of a patient support assembly. In other words, the patient can be rotated 180° to prone the patient to aid with respiratory disorders such as ARDS, or in order to perform surgical procedures or to permit the patient to lie face down on the support surface. The present invention permits full 180° rotation of a patient located on a patient support surface while providing spinal stability for spinal trauma patients.

The present invention provides a cantilevered design which cantilevers the entire patient support assembly from a foot end support assembly of the bed. No other support is required for rotation.

The present cantilevered design facilitates access to the head end of the bed which is substantially free from structural support. C-arm access is provided over the entire patient support surface for fill body imaging.

According to one aspect of the present invention, a bed includes a base having a first end and a second end, and a support assembly coupled to the first end of the base. The support assembly includes a rotatable drive mechanism. The bed also includes a patient support assembly having a support surface for supporting a patient The patient support assembly has a proximal end and a distal end spaced apart from the proximal end to define a longitudinal axis. The proximal end of the patient support assembly is coupled to the drive mechanism of the support assembly so that the distal end of the patient support assembly is cantilevered from the support assembly. The drive mechanism is configured to rotate the cantilevered patient support assembly about its longitudinal axis.

The bed includes a lifting mechanism coupled between the base and the support assembly. The lifting mechanism is configured to move the support assembly up and down relative to the base to raise and lower the patient support assembly relative to the base. The support assembly is pivotably coupled to the base about a pivot axis extending transverse to the longitudinal axis of the patient support assembly. A pivot mechanism coupled between the base and the support assembly, the pivot mechanism being configured to rotate the support assembly relative to the base about the pivot axis to move the support surface from a first generally horizontal position to an angled non-horizontal position.

In the illustrated embodiment, the support assembly includes a first support portion coupled to the base, a lifting mechanism coupled to the first support portion, and a movable frame coupled to the lifting mechanism for movement between an elevated position and a lowered position. The drive mechanism of the support assembly is coupled to the movable frame so that the patient support assembly is raised and lowered upon movement of the lifting mechanism. The lifting mechanism illustratively includes a rodless cylinder coupled to the first support portion. The rodless cylinder includes a movable carriage coupled to the movable frame. The lifting mechanism further includes a guide cylinder located adjacent the rodless cylinder. The guide cylinder includes a guide block slidable on the guide cylinder. The guide block is coupled to the movable frame. The illustrated lifting mechanism includes first and second rodless cylinders and first and second guide cylinders located on opposite sides of the movable frame.

The illustrated drive mechanism includes a annular rack rotatably coupled a front surface of the support assembly. The patient support assembly is coupled to the annular rack. The patient support assembly includes a pair of spaced apart support arms. First ends of the patient support arms are coupled to a plate which is coupled to the annular rack. The illustrated plate is cruciform-shaped. The first arms extend through the cruciform-shaped plate. The first ends of the support arms are connected to a second plate spaced apart from the cruciform-shaped plate.

In another illustrated embodiment, the support mechanism includes at least one receptacle coupled to the drive mechanism. The patient support assembly is separate from the support assembly and includes at least one arm configured to be coupled to the at least one receptacle to secure the patient support assembly to the drive mechanism.

According to one aspect of the present invention, a bed includes a base having a first end and a second end, and a support assembly coupled to of the base adjacent the first end. The support assembly includes a rotatable drive mechanism. The apparatus also includes a patient support assembly having a support surface for supporting a patient. The patient support assembly has a proximal end and a distal end spaced apart from the proximal end to define a longitudinal axis. The proximal end of the patient support assembly is coupled to the drive mechanism of the support assembly so that the distal end of the patient support assembly is cantilevered from the support assembly. The drive mechanism is configured to rotate the cantilevered patient support assembly about its longitudinal axis.

In the illustrated embodiment, the support assembly includes a first support portion coupled to the base, a lifting mechanism coupled to the first support portion, and a movable frame coupled to the lifting mechanism for movement between an elevated position and a lowered position. The drive mechanism of the support assembly is coupled to the movable frame so that the patient support assembly is raised and lowered by operation of the lifting mechanism.

The illustrated lifting mechanism includes a rodless cylinder coupled to the first support portion. The rodless cylinder includes a movable carriage coupled to the movable frame. The lifting mechanism further includes a guide cylinder located adjacent the rodless cylinder. The guide cylinder includes a guide block slidable on the guide cylinder. The guide block is coupled to the movable frame.

Also in the illustrated embodiment, the support assembly is pivotably coupled to the base about a pivot axis extending transverse to the longitudinal axis of the patient support assembly. A pivot mechanism is coupled between the base and the support assembly. The pivot mechanism is configured to rotate the support mechanism relative to the base about the pivot axis to move the support surface from a first generally horizontal position to an angled non-horizontal position. Therefore, the pivot mechanism is configured to adjust a position of the support surface relative to the base between a Trendelenburg position and a reverse Trendelenburg position.

The illustrated drive mechanism includes a annular rack rotatably coupled a front surface of the support assembly. The patient support assembly is coupled to the annular rack. The patient support assembly illustratively includes a pair of spaced apart support arms. First ends of the support arms are coupled to a plate, and the plate is coupled to the annular rack The plate is illustratively cruciform-shaped. The first ends of the support arms extend through the cruciform-shaped plate and are connected to a second plate spaced apart from the cruciform-shaped plate. The apparatus further includes a gear configured to engage the annular rack to rotate the rack relative to the front surface of the support assembly. The gear is coupled to a drive motor. A plurality of rotatable bearings is coupled to the front surface of the support assembly to hold the annular rack on the front surface of the support assembly.

In one illustrated embodiment, the support mechanism includes at least one receptacle coupled to the drive mechanism. The patient support assembly is separate from the support assembly and includes at least one arm configured to be coupled to the at least one receptacle.

The illustrated apparatus also includes a proning surface configured to be coupled to the patient support assembly. The proning surface is configured to support the patient in a prone position when the patient support assembly is rotated 180° about its longitudinal axis by the drive mechanism The proning surface includes a head-receiving portion.

According to another aspect of the present invention, a bed includes a base, a frame coupled to the base, first and second spaced apart arms coupled to the frame, first and second lifting mechanisms coupled to the first and second support arms, respectively, and a patient support surface coupled to the first and second lifting mechanisms. The lifting mechanisms are configured to move the patient support surface up and down relative to the first and second support arms.

In the illustrated embodiment, the first and second lifting mechanisms each includes first and second lifters, each lifter being separately controllable. The first and second lifters each include a pair of cylinders. Each cylinder includes a movable piston configured to control the location of the patient support surface relative to the first and second support arms. Each pair of cylinders includes first and second cylinders pivotably coupled to the support arms and first and second pistons, respectively, pivotably coupled to the patient support surface. The first and second pistons are pivotably coupled to the patient support surface about a single pivot axis, and the first and second cylinders are pivotably are coupled to the support arms about first and second spaced apart pivot axes, respectively.

The illustrated embodiment also includes first and second movable supports coupled to the first and second arms, respectively, by the first and second lifting mechanisms. The patient support surface is coupled to the first and second movable supports. The patient support surface includes a first portion pivotably coupled to the first movable support, a second portion pivotably coupled to the second movable support, and a locking mechanism configured to secure the first portion to the second portion. First and second air bladders are coupled to the first and second portions of the patient support surface, respectively, to support the patient. A proning surface includes a first portion pivotably coupled to the first movable support, a second portion pivotably coupled to the second movable support, and a locking mechanism configured to secure the first portion to the second portion to form the proning surface. First and second air bladders are coupled to the first and second portions of the proning surface, respectively, to support the patient in a prone position.

The illustrated embodiment includes a drive mechanism coupled to the frame and to the first and second arms to rotate the first and second arms about a longitudinal axis, and a proning surface coupled to the first and second arms. A controller is coupled to the first and second lifting mechanisms. The controller is configured to actuate the first and second lifting mechanisms to lift the patient support surface relative to the side arms. The controller is configured to elevate the patient support surface so that a center of gravity of the patient is at or above a center axis of the first and second support arms prior to rotation of the first and second arms about the longitudinal axis.

The illustrated controller is configured to actuate the first and second lifting mechanisms in alternating directions to provide rotation of the patient support surface relative to the first and second support arms about a longitudinal axis of the patient support surface. The controller is also configured to actuate the first and second lifters separately to move the patient support surface relative to the first and second arms about an axis transverse to the first and second arms between a Trendelenburg and a reverse Trendelenburg position. The controller is programmable to provide a sequence of treatments to the patient.

One illustrated embodiment includes a plurality of cushions on the patient support surface and the proning surface to provide therapy to a patient. The patient support surface includes a fixed portion coupled to the first and second arms and a removable backboard configured to support the patient. The backboard is configured to be located on the fixed portion of the patient support surface. The illustrated apparatus further includes a third lifting mechanism coupled between the base and the frame. The third lifting mechanism is configured to move the frame up and down relative to the base to raise and lower the patient support surface relative to the base.

According to yet another aspect of the present invention, a bed includes a base, and a support assembly coupled to the base. The support assembly includes a rotatable drive mechanism. The apparatus also includes a patient support surface coupled to the drive mechanism of the support assembly so that the drive mechanism rotates the patient support surface about its longitudinal axis, a monitoring device having an output signal indicating a condition of the patient, and a controller coupled to the monitoring device and the drive mechanism to control a frequency of rotation of the patient support surface in response to the output signals from the monitoring device.

Additional objects, features, and advantages of the invention will become apparent to those skilled in the art upon consideration of the following detailed description of the illustrated embodiment exemplifying the best mode of carrying out the invention as presently perceived.

BRIEF DESCRIPTION OF THE DRAWINGS

The detailed description particularly refers to the accompanying figures in which:

FIG. 2 is a perspective view, with portions broken away, illustrating a base and a patient support surface support assembly located at a foot end of the bed to control movement of the patient support surface;

FIG. 3 is a perspective view, with portions broken away, illustrating additional details of the support assembly of the present invention;

DETAILED DESCRIPTION OF THE DRAWINGS

Figure 1:
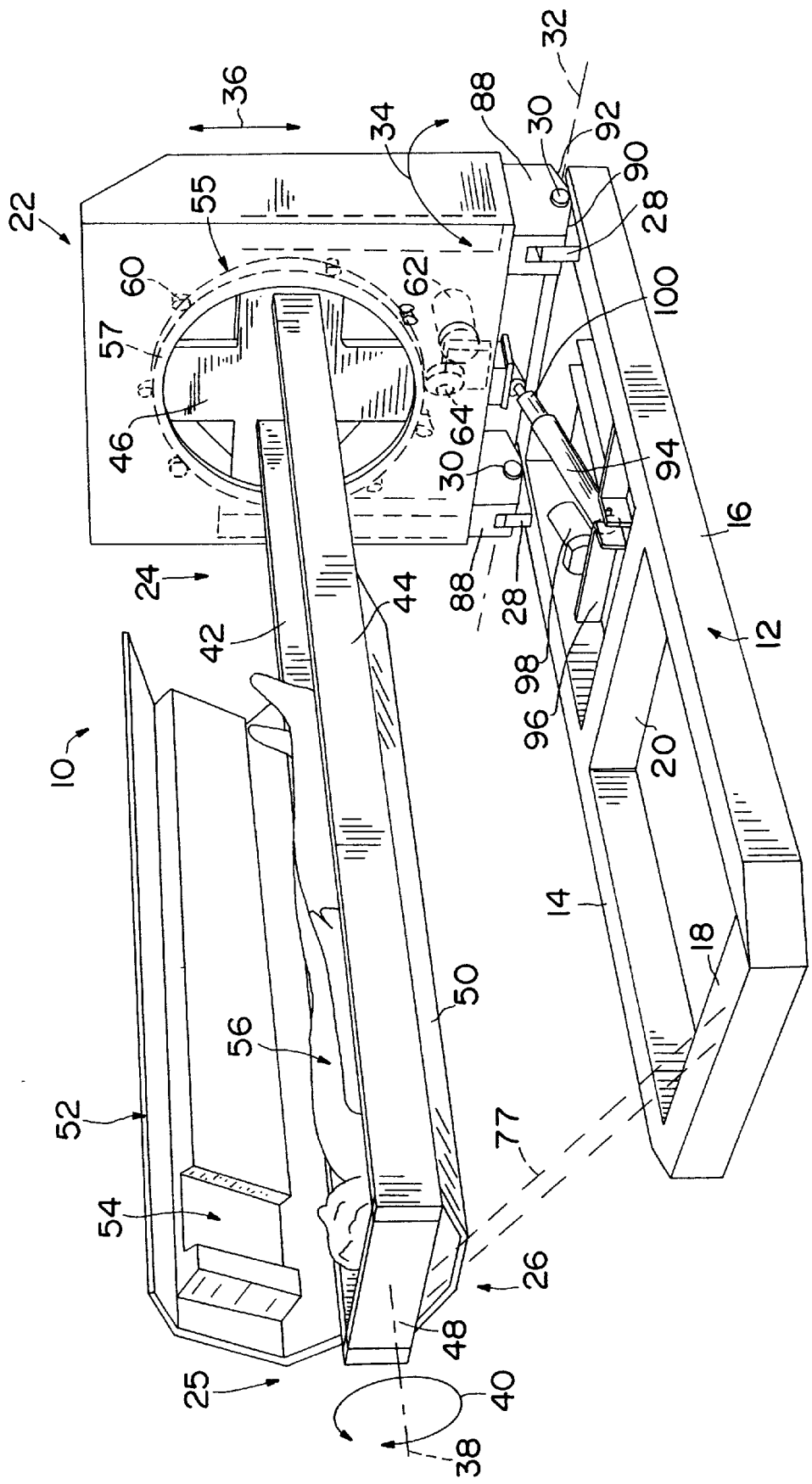
FIG. 1 is a perspective view illustrating a proning bed of the present invention.

Referring now to the drawings, FIG. 1 illustrates a bed 10 having a base 12 which includes opposite side members 14 and 16 and cross members 18 and 20 extending between side members 14 and 16. A support assembly 22 is located at a foot end 24 of bed 10. Support assembly 22 supports a patient support assembly 26 in a cantilevered fashion. Therefore, the head end 25 of bed 10 is open to facilitate access to the patient 56.

Support assembly 22 is pivotably coupled to pivot blocks 28 of base 12 by pivot connections 30. Therefore, support assembly 22 can pivot about axis 32 in the directions of double-headed arrow 34. As discussed in detail below, the support assembly 22 is movable up and down in the direction of double-headed arrow 36 to raise and lower the height of patient support assembly 26. Also as discussed below in detail, support assembly 22 can rotate the patient support assembly 26 about its longitudinal axis 38 as indicated by double-headed arrow 40. Support assembly 22 can rotate the patient support assembly 26 in either direction a full 360°.

Patient support assembly 26 includes a pair of horizontally extending arms 42 and 44 which are coupled to a cruciform-shaped plate 46 of support assembly 22. Arms 42 and 44 extend away from support assembly 22 in a cantilevered fashion. An end beam 48 extends between arms 42 and 44 at a distal end of patient support assembly 26. A patient support surface 50 is coupled between arms. When it is desired to rotate a patient, a proning support surface 52 is also coupled between arms 42 and 44. Proning support surface 52 includes a recess 54 for receiving the head of a patient 56. Support surfaces 50 and 52 are shown in an illustrative representation only. It is understood that support surfaces 50 and 52 will include selective placement of foam, air bladders, fluidized bladders, or other suitable support surfaces to reduce pressure on the patient 56 and/or support an unstable spine of the patient 56. The support surfaces 50 and 52 may include contoured support surfaces to minimize pressure on the patient. Layers of air and beads can be positioned over the contoured support surfaces. A vacuum can be selectively applied to the bead packs to further conform the support surfaces to the patient.

Cruciform 46 is coupled to a drive mechanism 55 including rotatable, annular rack 57 which is held in place on a front surface 58 of support assembly 22 by rotatable bearings 60 which are coupled to front surface 58. Cruciform 46 includes four arms which are each secured to the annular rack 57. A motor 62 and gear 64 are located on support assembly 22. Gear 64 engages annular rack 57 to rotate the annular rack 57 relative to the front surface 58. Therefore, the support arms 42 and 44 coupled to the cruciform also rotate in the direction of double-headed arrow 40. As illustrated in FIGS. 2 and 3, the arms 42 and 44 extend through the cruciform 46 and are then welded to the cruciform 46. Arms 42 and 44 are also welded to a rear support plate 66. Extension sections 68 are welded between the support plate 66 and the cruciform 46 at locations between the support arms 42 and 44.

The support assembly 22 includes a movable frame 70 which is movable relative to outer supports 72. FIG. 2 illustrates the frame 70 in an upwardly extended position.

Opposite outer supports 72 each include a rodless cylinder 74 having a movable carriage 76. Movable carriage 76 is coupled to a sidewall 78 of movable frame 70 by fasteners 80. A guide cylinder 82 is located adjacent each rodless cylinder 74. A guide block 84 slides over each cylinder 82. Guide block 84 is coupled to sidewall 78 of frame 70 by fasteners 86.

Illustratively, rodless cylinders 74 are Lintra® rodless cylinder available from Norgren located in Rockford, Ill. An air supply is used to control movement of the carriages 76 on the rodless cylinders 74 to move the movable frame 70 of the support assembly 22 up-and down in the directions of double-headed arrow 36. Since the annular rack 57, the cruciform 46 and the patient support assembly 26 are all coupled to the movable frame 70, the support surface 26 moves up and down in the direction of double-headed arrow 36 with the movable frame 70. Illustratively, the cylinders 74 provide and 8–9 inch lift. It is understood that hydraulics, lead screws, or other suitable lifting mechanisms can be used with the present invention.

The cantilevered design of the present invention advantageously suspends the patient support surface 26 from the support assembly 22. This permits full body C-arm access. In addition, a head end 25 of the bed is accessible for performing procedures on the patient 56. A support bar 77 can extend between the head end 25 of patient-support surface 26 and base 12 if desired. The support bar 77 can be moved into the support position engaging support surface assembly 26 while the patient 56 is on support surface 50. The support bar 77 can be removed from support surface assembly 26 for C-arm access or rotation.

Figure 4:
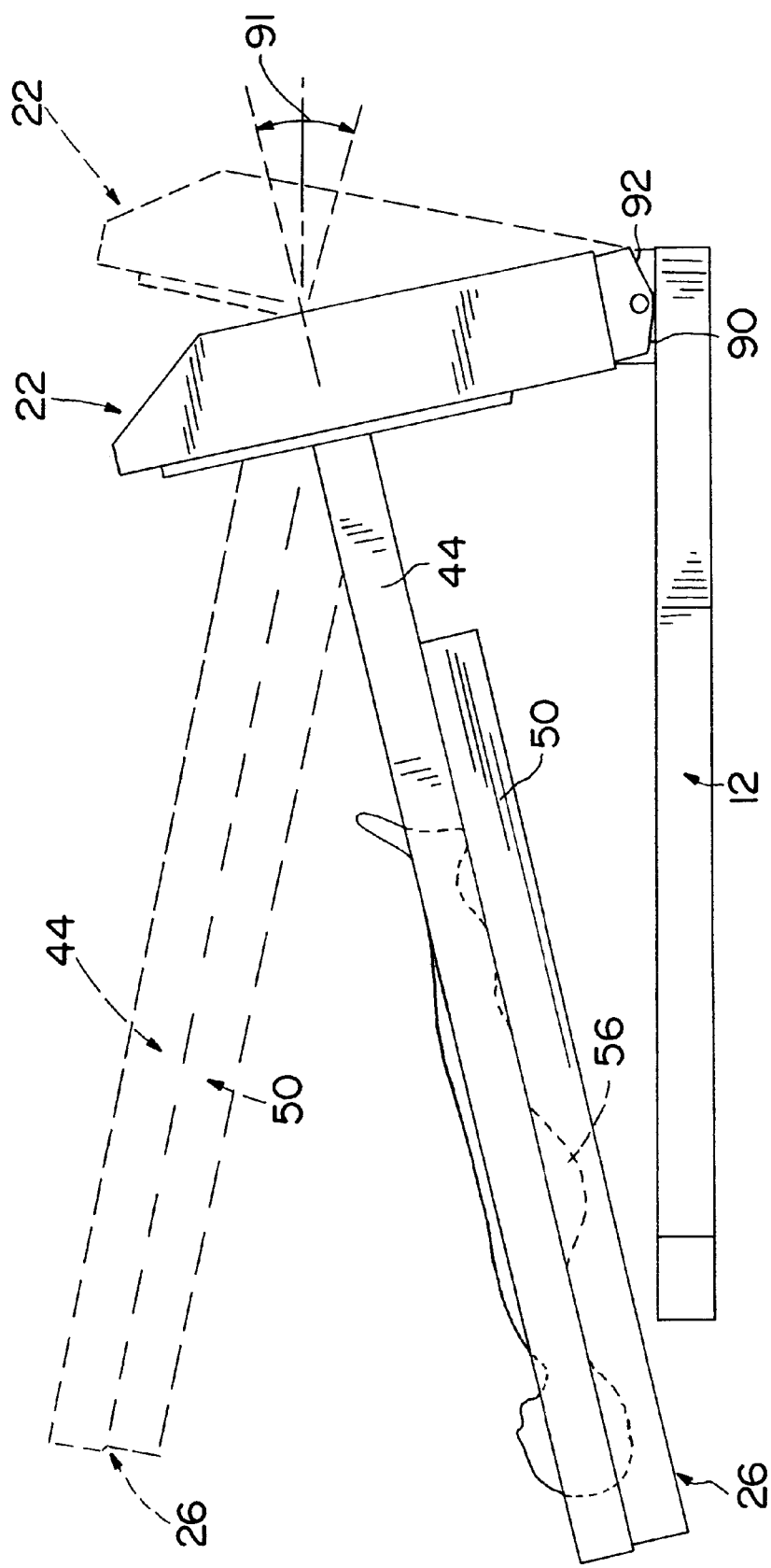
FIG. 4 is a side elevational view illustrating movement of the support assembly to position the patient support surface in either a Trendelenburg or a reverse Trendelenburg position.

The support assembly 22 is coupled to base 12 by blocks 88. Blocks 88 include a front angled stop 90 and a rear angled stop 92 which limit pivotable movement of the support assembly 22 relative to the base 12. As illustrated in FIG. 4, the support assembly 22 is pivotable relative to base 12 to move the patient support assembly 26 between a Trendelenburg position illustrated in solid lines in FIG. 4 to a reverse Trendelenburg position illustrated in dotted lines in FIG. 4. Illustratively, the pivotable movement is about +/−15° relative to horizontal in either direction as illustrated by angles 91 in FIG. 4. Front stop 90 engages base 12 when the patient support surface is in the Trendelenburg position shown in solid lines in FIG. 4. Second stop 92 engages the base 12 when the support assembly is in the reverse Trendelenburg position as shown in dotted lines in FIG. 4.

Pivotable movement of support assembly 22 about axis 32 is controlled by a cylinder 94 pivotably coupled to a cross member 96 which extends between arms 14 and 16 of base 12. A fluid source 98 is also coupled to cross member 96 to control movement of a piston 100 relative to cylinder 94 between an extended position and a retracted position. Piston 100 is pivotably coupled to support assembly 22. Therefore, retraction of piston 100 causes movement of the support assembly 22 forward to the Trendelenburg position. Extension of piston 100 causes pivotable movement of the support assembly 22 to the reverse Trendelenburg position.

Figure 5:
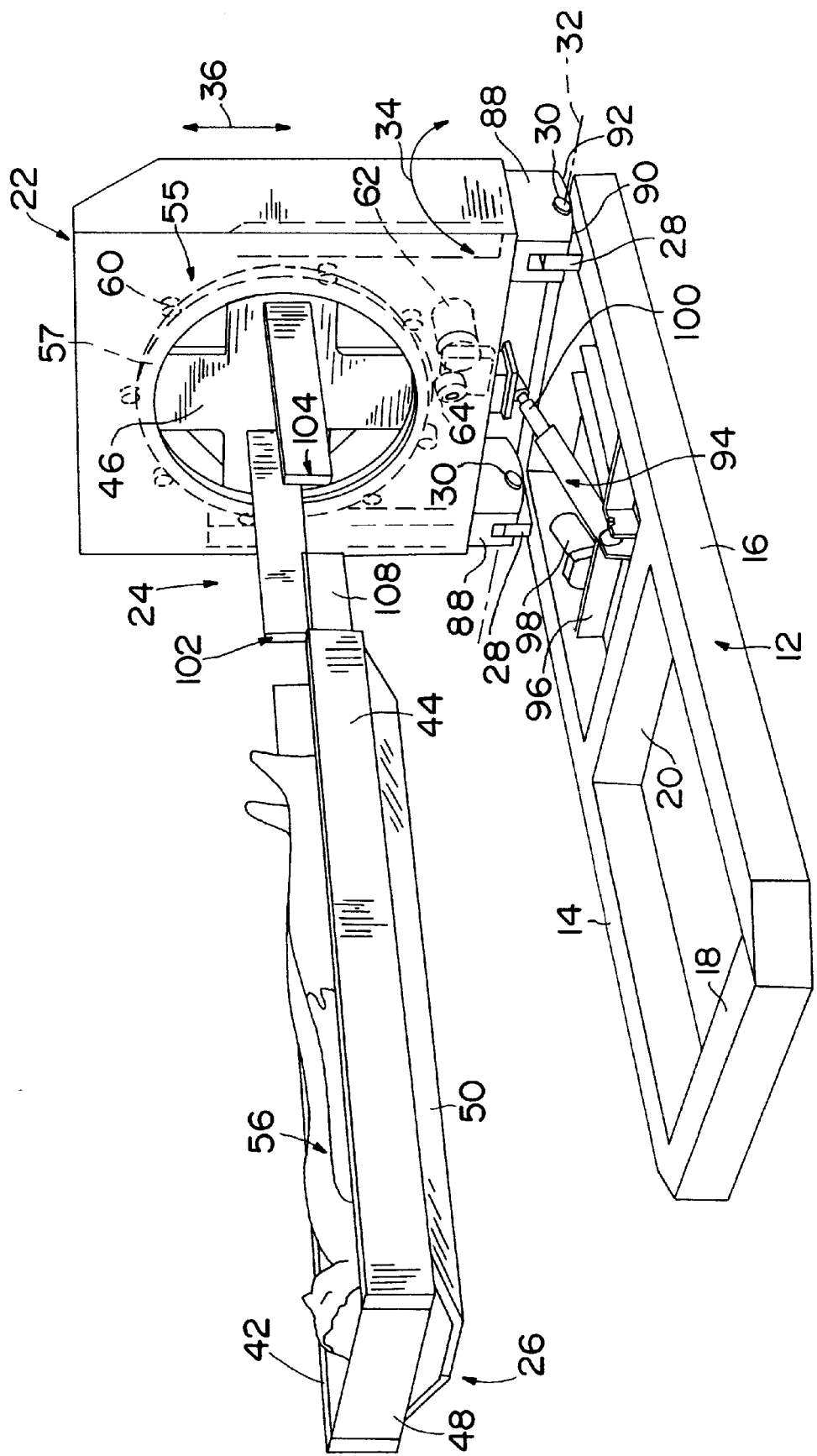
FIG. 5 is a perspective view illustrating another embodiment of the present invention in which a modular patient support assembly is configured to be coupled to receptacles on the support assembly.

Although the side arms 42 and 44 of the patient support assembly 26 are shown as solid arms in FIG. 1, it is understood that the side arms 42 and 44 may be shorter pieces cut off adjacent support assembly 22 as illustrated by arms 102 and 104 in FIG. 5. Since arms 102 and 104 are illustratively hollow receptacles, the remainder of the patient support assembly 26 includes arm extensions 106 and 108 which slide into the open ends of receptacle arms 102 and 104 extending from support assembly 22. Therefore, a patient could be transported directly from a trauma situation on the patient support surface 50 using suitable handles (not shown). The patient support assembly 26 and surface 50 may then be attached to the open ends of arms 102 and 104 and secured in position to form a cantilevered support surface 26 for the patient 56 without having to move the patient 56 from the support surface 50. Operation of the bed is then as described above.

The bed can be programmed to provide rotational therapy to the patient. The bed can also be used to prone the patient 56 so that the patient lies face down on the proning support surface 52.

In FIGS. 6–15, these elements referenced by numbers from FIGS. 1–5 perform the same or similar function. Patient support assembly includes a lower set of doors 110 and an upper set of doors 112. Lower set of doors 110 supports the patient support surface 50 for holding the patient in a supine position. Doors 110 and 112 are pivotably coupled to lifting apparatus 114 and 116. A first lifting apparatus 114 is coupled to arm 42, and a second lifting apparatus 116 is coupled to arm 44. Each lifting apparatus 114 and 116 includes an outer rectangular support 118 having a top surface 120 and a bottom surface 122. Each lifting apparatus 114, 116 further includes first and second lifters or lifting cylinder assemblies 124 and 126 located within side arms 42, 44, respectively. The first and second cylinder assemblies 124 and 126 each include a pair of cylinders 128, 130 which are coupled to arms 42, 44 by pivot connections 132 and 134, respectively. Cylinders 128 and 130 include pistons 136 and 138, respectively, which are pivotably coupled to top surface 120 of movable support 118 at locations 140. Illustratively, cylinders 128, 130 are hydraulic cylinders controlled by a suitable controller located within support assembly 22. Lines for controlling cylinders 128, 130 can be run through the arms 142, 144 to minimize line clutter.

Figure 6:
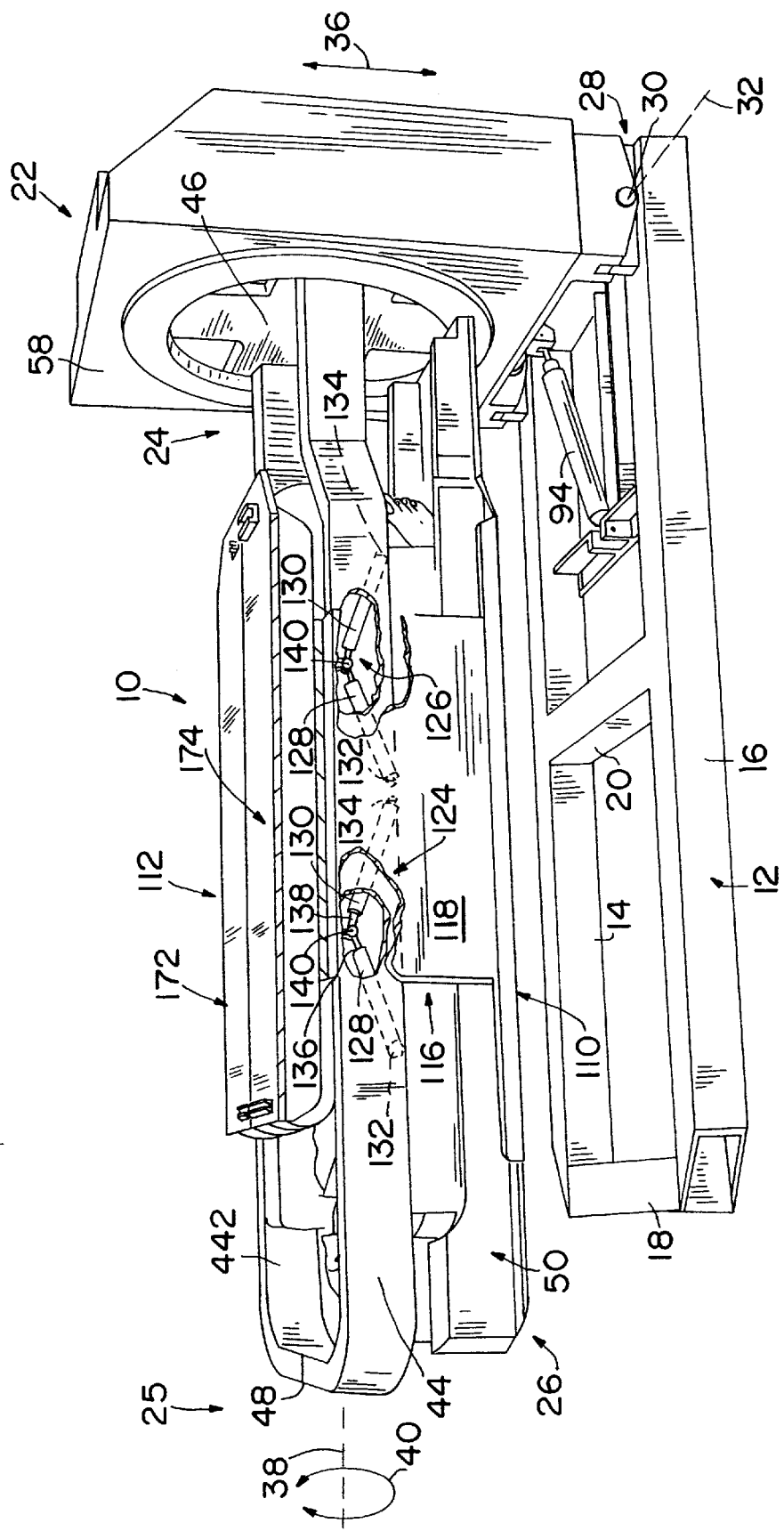
FIG. 6 is a perspective view illustrating a proning bed of the present invention, with a patient on a support surface in a supine position.
Figure 10:
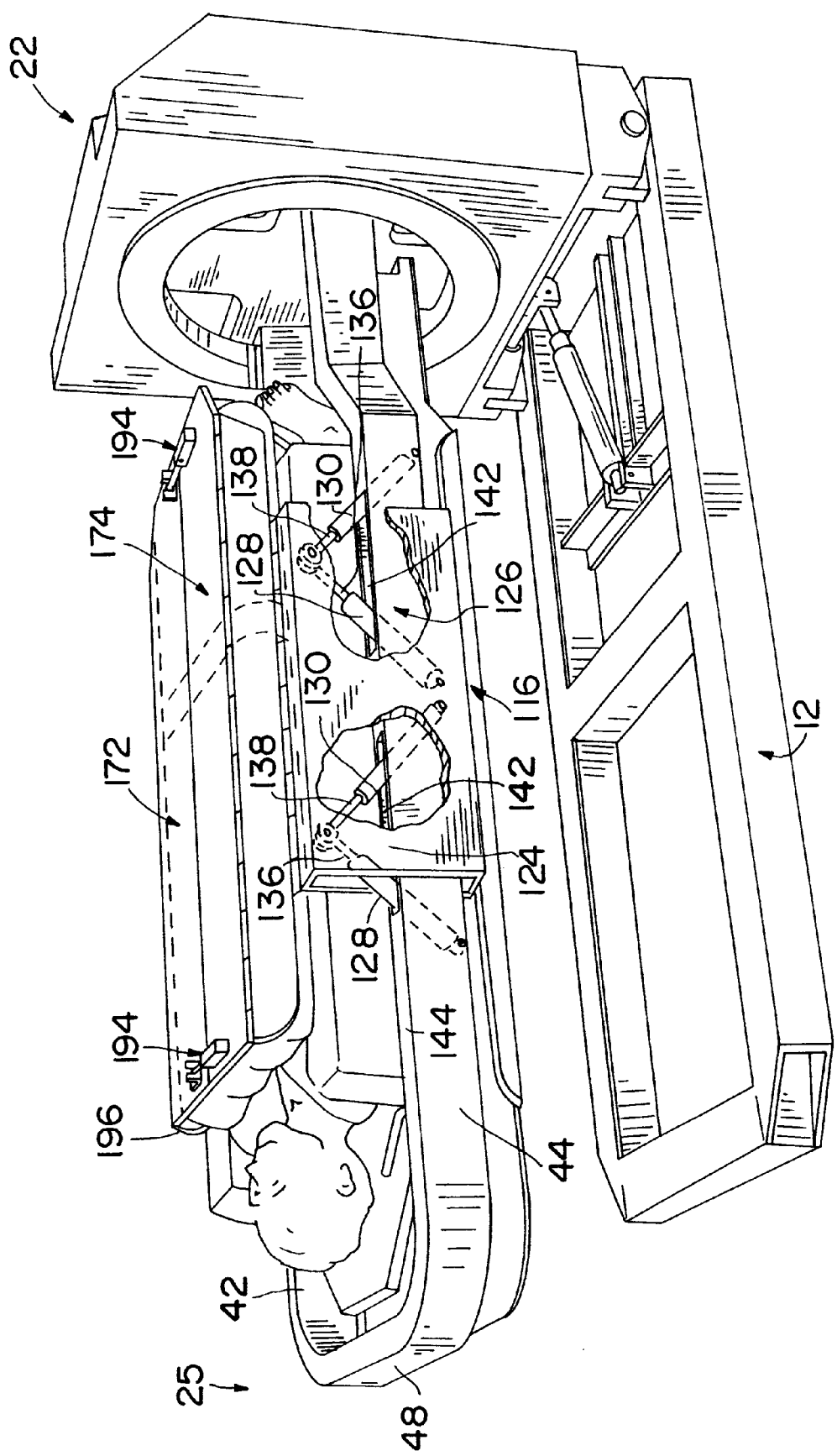
FIG. 10 is a perspective view similar to FIG. 6, illustrating the patient support surface in its raised position relative to the side arms of the bed.

The pistons 136, 138 are movable from a retracted position illustrated in FIG. 6 to an extended position illustrated in FIG. 10. In the retracted positions, pistons 136 and 138 position the support surface 50 at a lowermost position relative to arms 42 and 44 of the frame. In the extended position, the pistons 136 and 138 lift the movable support 118 and the patient support surface 50 coupled thereto upwardly to the position shown in FIG. 10. Arms 42 and 44 each are configured to include apertures 142 shown in FIG. 10 to permit the cylinders 128, 130 and pistons 136, 138 to move upwardly past a top surface 144 of frame arms 42, 44.

Figure 7:
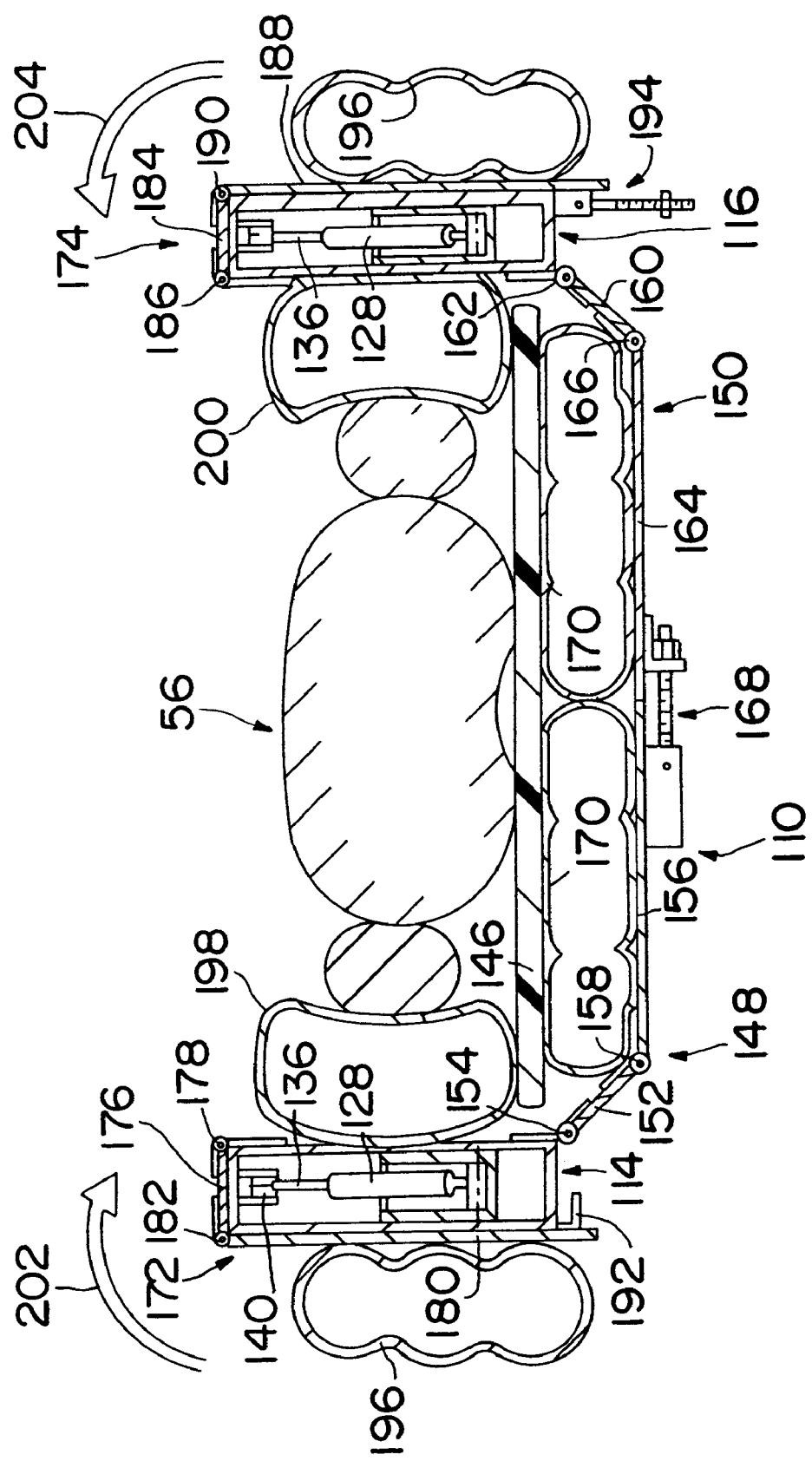
FIG. 7 is a sectional view taken through the patient support assembly of FIG. 1 illustrating top doors in an open position.

The bed 10 is configured so that a patient can be transported from a remote trauma location and positioned directly on the bed as illustrated in FIG. 7. Illustratively, the patient is transported to the bed 10 on a backboard 146. Illustratively, the backboard 146 may include air bladders, foam padding, and/or contoured sections to facilitate transport of the patient and to provide a pressure reducing surface when the backboard 146 is located on the bed 10. The backboard 146 may illustratively include a self-inflating surface, such as a Therm-A-Rest® mattress, for use in the field. When the backboard 146 is loaded into the bed 10, connectors are provided for coupling air bladders on the backboard to the air supply system and valves already located on the bed 10. Connectors are also provided for coupling the backboard 146 to the bed 10 mechanically and electrically.

As illustrated in FIG. 7, the bottom door assembly 110 includes a first door 148 pivotably coupled to the first lifting mechanism 114 and a second door 150 pivotably coupled to the second lifting mechanism 116. The first door 148 includes a first section 152 pivotably coupled to the first lifting mechanism 114 by hinge 154 and a second portion 156 pivotably coupled to the first portion 152 by hinge 158. Second door 150 includes a first portion 160 pivotably coupled to the second lifting mechanism 116 by hinge 162 and a second portion 164 pivotably coupled to the first portion 160 by hinge 166. Latches 168 are used to secure the first and second doors 148 and 150 in a closed position illustrated in FIG. 7 to provide a support for the backboard 146. Illustratively, a pair of air bladders 170 are located on an inner surface of doors 148 and 150 to provide a support for backboard 146. Alternatively, the patient can be situated directly on the air bladders 170 if the patient has not been transported to the bed on the backboard 146.

The proning doors 112 similarly include a first door 172 and a second door 174 shown in an open position in FIG. 7. Door 172 includes a first portion 176 pivotably coupled to first lifting apparatus 114 by hinge 178. Door 172 further includes a second portion 180 pivotably coupled to first portion 176 by hinge 182. Door 174 includes a first portion 184 coupled to second lifting apparatus 116 by hinge 186 and a second portion 188 pivotably coupled to first portion 184 by hinge 190. A first latch portion 192 is coupled to second door portion 180 of door 172, and a second latch portion 194 is coupled to second door portion 188 of second door 174. Air bladders 196 are also coupled to second door portions 180 and 188. FIG. 7 also illustrates a pair of inner inflatable side bladders 198 and 200 located along opposite sides of the patient 56.

FIG. 7 illustrates the top doors 172 and 174 in an open position. In the open position, first door portions 176 and 184 rest upon top surface 120 of the first and second lifting apparatus 114, 116, respectively. Therefore, the second door portions 180 and 188 can lie adjacent outer surfaces 118 of the first and second lifting apparatus 114 and 116, respectively, to conserve space. Air bladders 196 may be deflated to conserve additional space.

Figure 8:
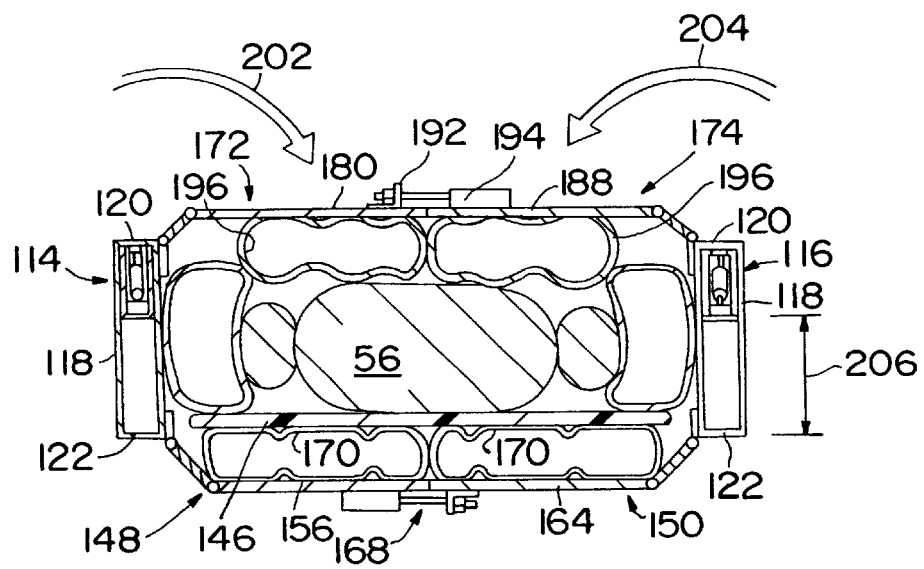
FIG. 8 is a sectional view through the patient support assembly of FIG. 6 with the proning doors in a closed and latched position and with a lifting apparatus on each side of the patient support surface, each lifting apparatus being adjusted to move the patient support surface to its lowermost position relative to support arms of the bed.

After the patient is transported to the bed 10 from an injury site or other location on backboard 146, the patient 56 and the backboard 146 are loaded into the bed 10 as illustrated in FIG. 7 with the patient in the supine position. If it is desired to prone the patient 56 for a medical procedure or therapy, the doors 172 and 174 are closed in the direction of arrows 202 and 204 of FIG. 7, respectively. Once the doors are moved to a closed position illustrated in FIG. 6 and 8–10, latches 192 and 194 are connected to secure the doors 172 and 174 together. It is understood that any type of latch mechanism can be used to hold the doors 172 and 174 in the closed position. As shown in FIG. 8, the air bladders 196 are configured to lie over the patient 56 when the doors 172 and 174 are closed.

In FIG. 8, the pistons 136 and 138 of cylinders 128 and 130, respectively, are in the retracted position shown in FIG. 6. Therefore, the arms 42 and 44 are located adjacent top surface 120 of support 118 of the first and second lifting apparatus 114 and 116. Therefore, bottom surfaces of arms 42 and 44 are spaced apart from a bottom surface 122 of first and second lifting apparatus 114 by a distance 206. In the position of FIGS. 6 and 8, the patient 56 is located at the lowermost support position relative to arms 42 and 44.

Figure 9:
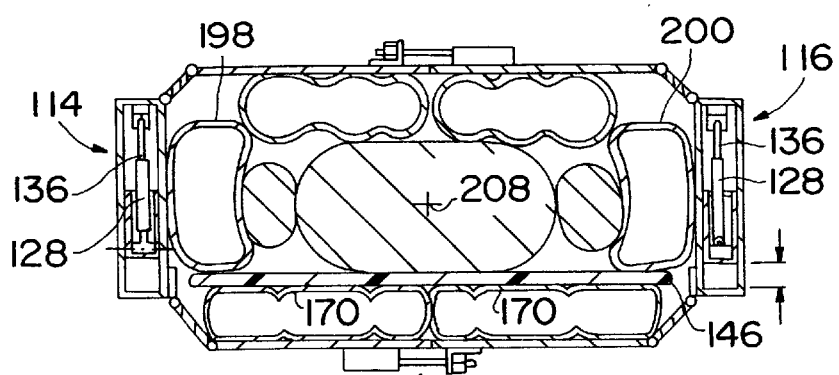
FIG. 9 is a sectional view similar to FIG. 8 in which the lifting apparatus are actuated to move a patient support surface upwardly relative to side support arms of the bed.
Figure 11:
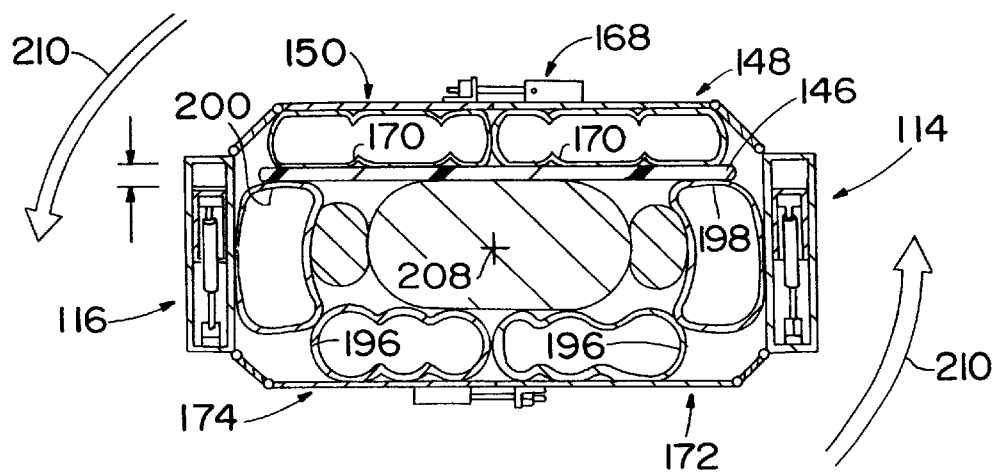
FIG. 11 is a sectional view taken through the patient support surface of FIG. 5, after the bed is operated to rotate the support surface, thereby turning the patient over to a prone position.

When it is desired to rotate or prone the patient, it is desirable to move the patient's center of gravity to a location above a pivot axis 38 of patient support assembly 26. Therefore, before rotating the patient 56, the first and second lifting apparatus 114 and 116 are actuated to extend the pistons 136 and 138 from cylinders 128 and 130 of the first and second cylinder arrangements 124 and 126. By extending the pistons 136 and 138, the top surfaces 120 of supports 118 of the lifting apparatus 114 and 116 move upwardly to the position illustrated in FIGS. 9 and 10. FIG. 9 shows that the distances between the bottom surfaces arms 42 and 44 is closer to the bottom surfaces 122 of supports 118 lifting apparatus 114 and 116 in the FIG. 9 configuration. The patients center of gravity 208 is at or slightly above the location of pivot axis 38. This positioning of patient 56 facilitates the rotating operation and provides less of a falling sensation for the patient 56 as rotation begins.

A controller of the present invention is configured to position the patient properly for proning automatically. A caregiver enters the patient's height and weight using an input device, and then the controller calculates a location of the center of gravity of the patient using known algorithms. The controller then sends appropriate control signals to the cylinders 128 and 130 to lift the patient a desired distance. Once the patient is positioned as illustrated in FIGS. 9 and 10, the controller actuates the drive motor and gear which drives the annular ring and rotates the cruciform 46 and arms 42 and 44 in the direction of arrows 210 in FIG. 11 until the patient has been proned. Once in the prone position of FIG. 11, latches 168 are opened to permit doors 148 and 150 to be moved away from the patient 56. Backboard 146 can then be removed to expose a back of the patient 56. Before the patient is moved to the prone position shown in FIG. 11, an appropriate head support member (not shown) is coupled to the proning doors 112 to support the patient's head and while in the prone position. Alternatively, the length of doors 172 and 174 may be extended and formed to include a recess for receiving the patient's face.

Figure 12:
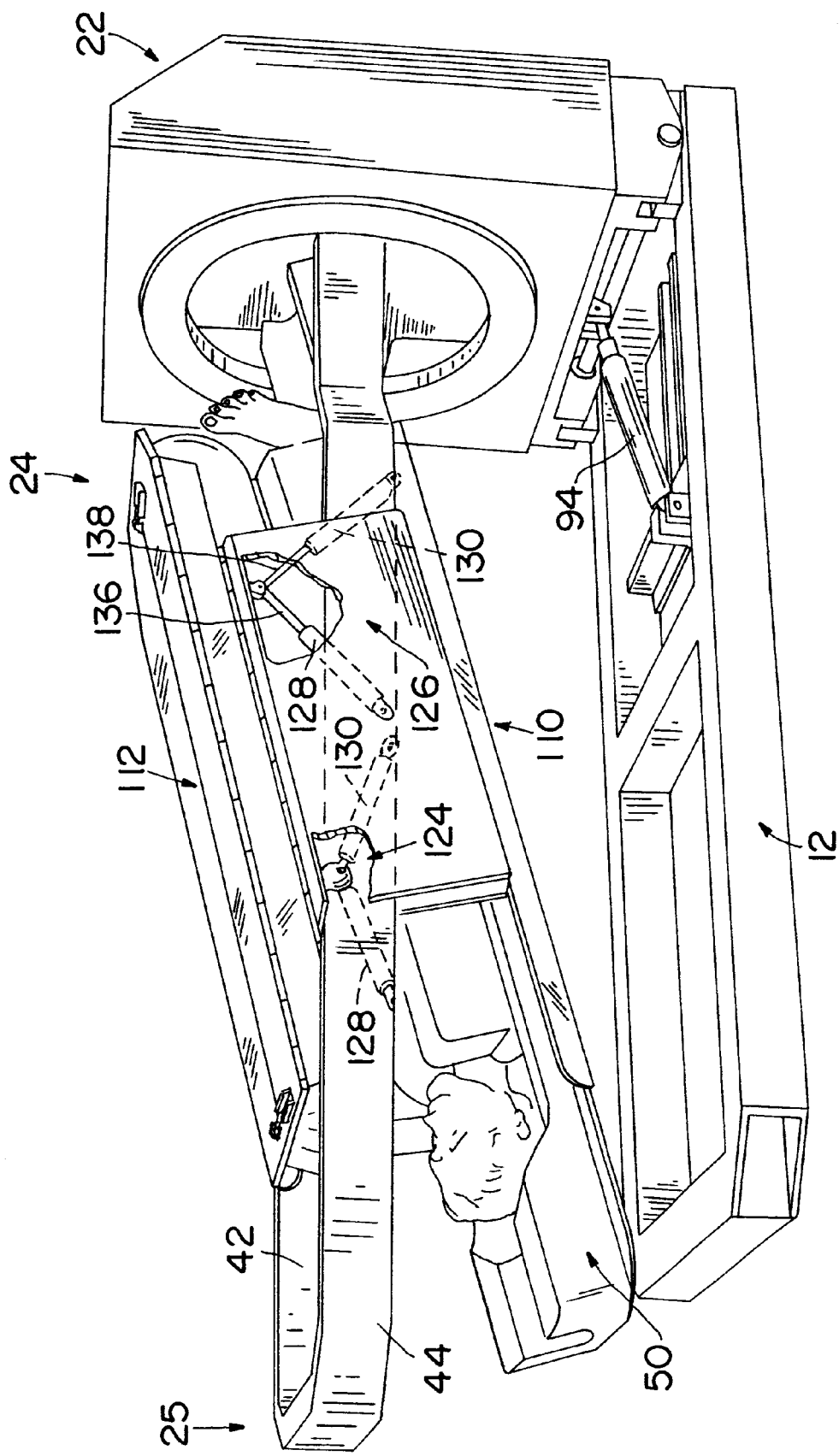
FIG. 12 is a perspective view illustrating the patient support surface of the bed moved to a Trendelenburg position.
Figure 13:
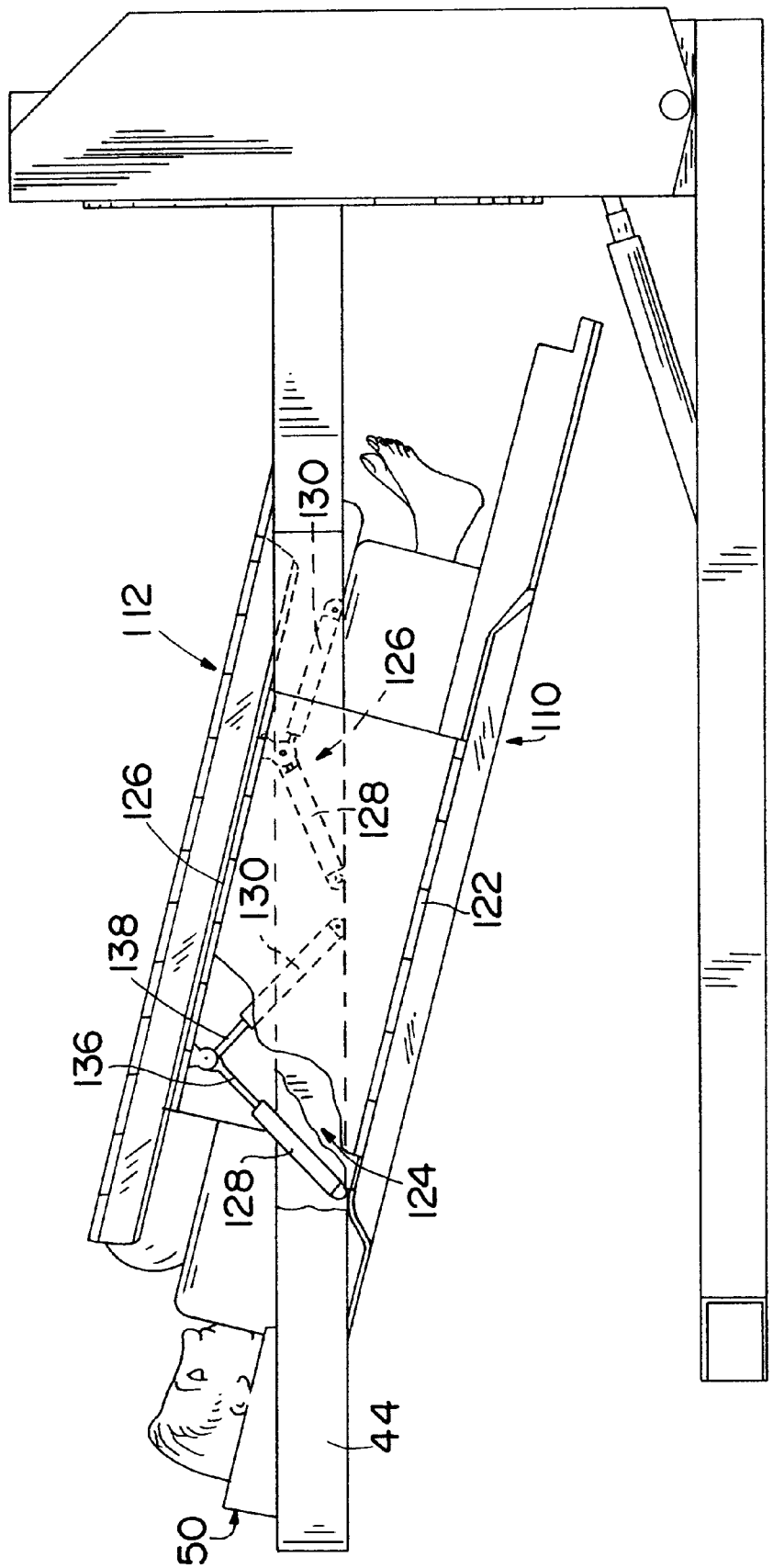
FIG. 13 is a perspective view of the bed of the present invention with the patient support surface in a reverse Trendelenburg position.

As shown in FIGS. 12 and 13, lifting apparatus 114, 116 may also be used for moving the patient support surface 50 from a Trendelenburg position shown in FIG. 12 to a reverse Trendelenburg position shown in FIG. 13. Using the first and second lifting apparatus 114, 116 in this manner eliminates the need for a separate cylinder 94 and a pivotable connection between support 22 and base 12. In other words, the support 22 may be rigidly coupled to base 12 when the first and second lifting apparatus 114 and 116 are used for the Trendelenburg and reverse Trendelenburg positioning.

As shown in FIG. 12, when the pistons 136 and 138 of the first pair of cylinders 124 are in the fully retracted position and the pistons 136 and 138 of the second set of cylinders 126 are in the fully extended position, the patient support surface 50 moves to a Trendelenburg position. Conversely, when the pistons 136 and 138 of the first set of cylinders 124 are moved to fully extended and the pistons 136, 138 and the second set of cylinders 126 are moved to the fully retracted position, the patient support 50 moves to a reverse Trendelenburg position as shown in FIG. 13.

Therefore, the lifting apparatus 114, 116, could also be used to provide rotation of patient 56 about a lateral axis perpendicular to longitudinal axis 38 and the patient 56. In other words, the lifting apparatus 114, 116 can be used to move the patient back and forth between the FIG. 12 position and the FIG. 13 position.

Figure 14:
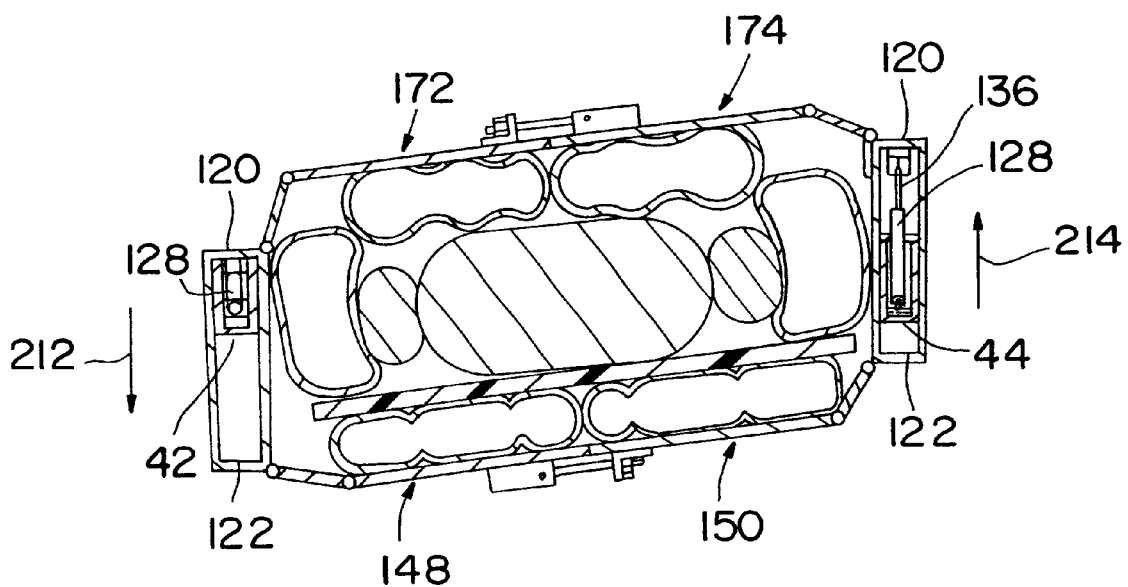
FIGS. 14 and 15 illustrate actuation of a lifting mechanisms on opposite sides of the bed for providing patient rotation using only the lifting mechanisms actuated in opposite, alternating directions.
Figure 15:
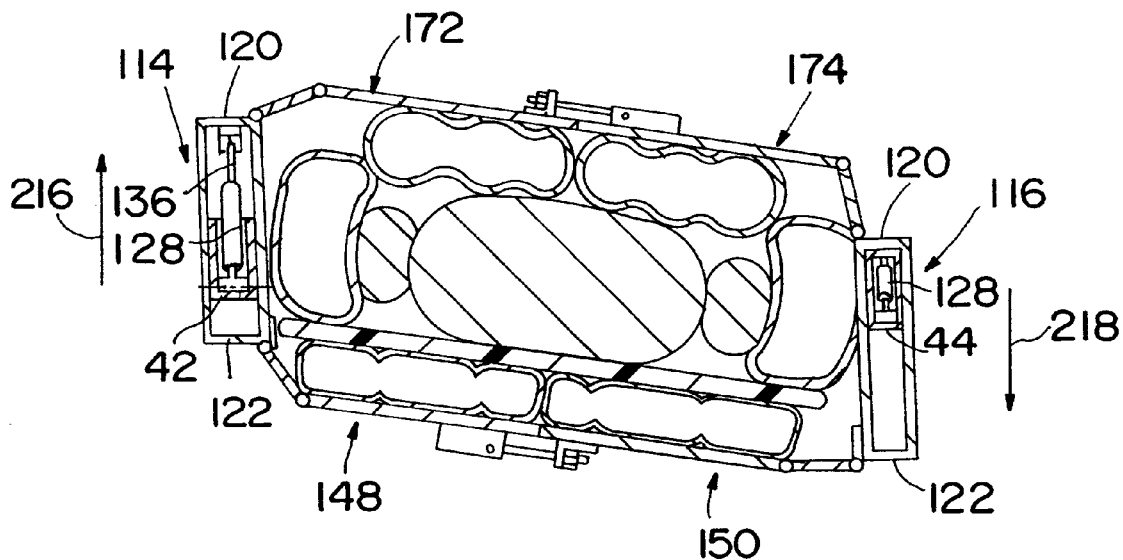

As shown in FIGS. 14 and 15, the first and second lifting apparatus 114, 116 may also be used to provide limited rotational therapy for the patient 56 about axis 38. The main drive motor within support assembly 22 can also be used for rotational therapy. In other words, the entire frame assembly 42, 44, and 48 may be rotated back and forth about axis 38 to provide rotational therapy for the patient. To provide the rotational therapy using only the first and second lifting apparatus 114, 116, the following sequence is used. The pistons 136 and 138 of the first and second cylinder pairs 124 and 126 in lifting apparatus 114 are moved to the retracted position while the pistons 136 and 138 of the cylinders 124 and 126 of lifting apparatus 116 are moved to the extended position as shown in FIG. 14. This causes the support 118 of first lifting apparatus 114 to move downwardly in the direction of arrow 212 and the support 118 of second lifting apparatus 116 to move upwardly in the direction of arrow 214. Next, the pistons 136 and 138 of the cylinder pairs 124 and 126 of lifting apparatus 114 are extended to move the support 118 of lifting apparatus. 114 upwardly in the direction of arrow 216 of FIG. 15. Simultaneously, the pistons 136 and 138 of the cylinder pairs 124 and 126 of lifting apparatus 116 are retracted to move the support 118 of second lifting apparatus 116 downwardly in the direction of arrow 218. Therefore, as shown in FIGS. 14 and 15, rotational therapy can be provided to the patient 56 by alternately extending and retracting, in opposite timing, the pistons 136 and 138 of the cylinder pairs 124 and 126 of first and second lifting apparatus 114 and 116.

Figure 16:
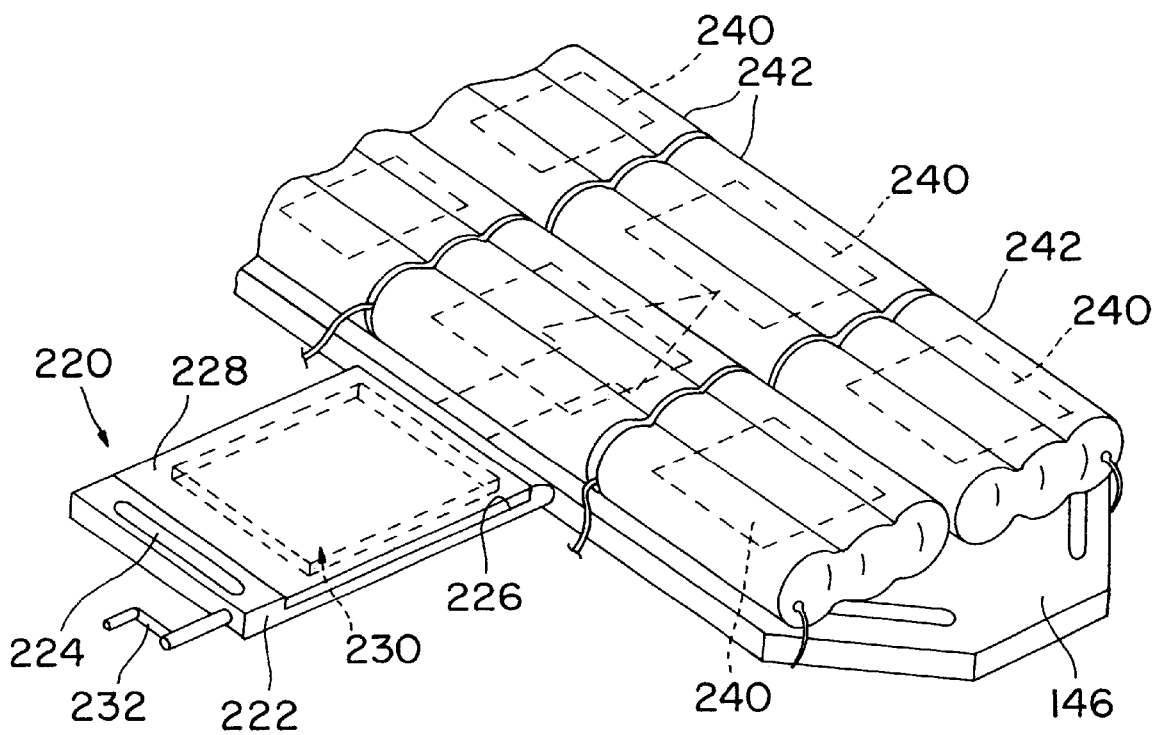
FIG. 16 illustrates insertion of an x-ray cassette below the patient support surface of the present invention.
Figure 17:
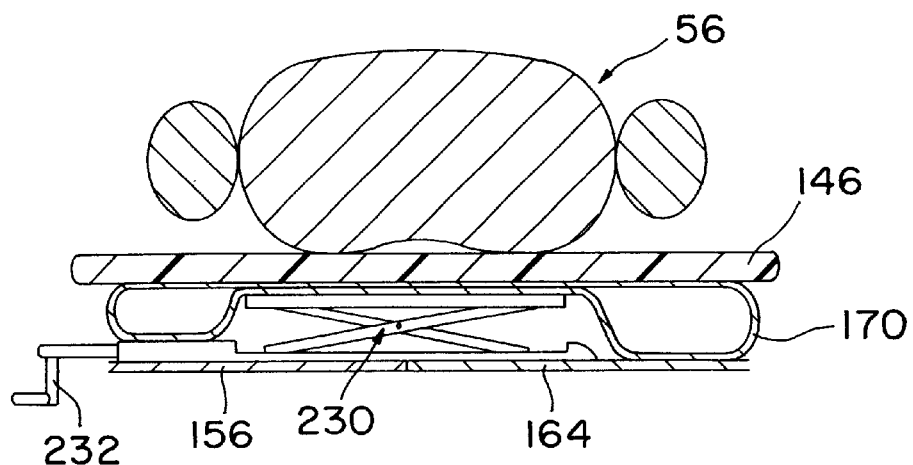
FIG. 17 is a sectional view illustrating actuation of the x-ray cassette holder to move the x-ray cassette close to a patient support surface to improve imaging.

FIGS. 16 and 17 illustrate an x-ray carriage 220 including a frame 222 having a handle 224 and a recessed portion 226 configured to receive an x-ray cassette 228. Carriage 220 also includes a lifting mechanism 230 best illustrated in FIG. 17 which is operated by a crank 232. The carriage 220 is designed to be inserted below bladders 170 and backboard 146 to lie on doors 156 and 164. Appropriate openings (not shown) are formed in door sections 152 or 160 to permit insertion of the carriage 220. Once the carriage 220 is positioned at a desired location, lifting apparatus 230 is actuated to lift the x-ray cassette 228 upwardly as shown in FIG. 17. The bladder 170 above the x-ray cassette 228 is deflated to permit the x-ray cassette 228 to be moved upwardly against a bottom surface of backboard 146. By moving the x-ray cassette 128 closer to the bottom surface of backboard 146, imaging is improved.

In another embodiment of the present invention, the apparatus includes surface pressure sensing integrated into the patient support surface. Specifically, an array of capacitive pressure sensors 240 are coupled to a top surface of patient support bladders 242 as shown in FIG. 16. Foam support surfaces may be located in the air bladders 242, if desired. As a patient 56 changes positions on the support bladders 242, or is rotated within the bed 10, pressure within each bladder 242 is adjusted based on inputs from the pressure sensor array 240 to keep interface pressure below capillary closure pressure or at as low a pressure as possible.

Figure 18:
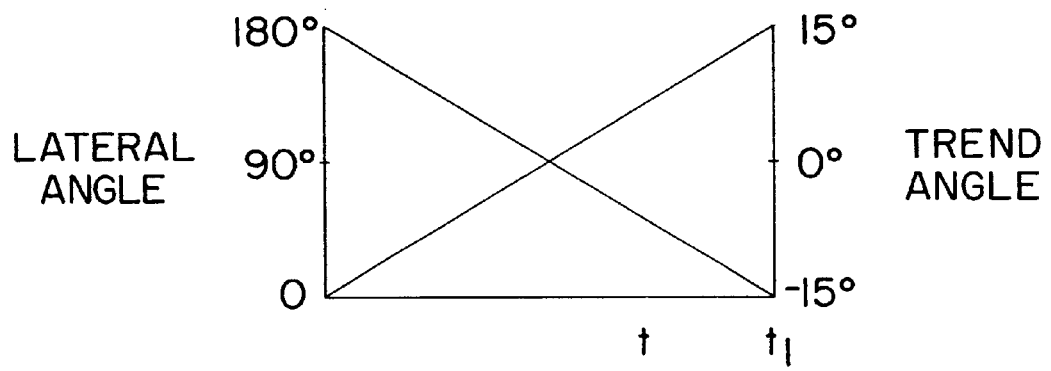
FIG. 18 is a chart illustrating rotation of the patient support surface about both a lateral axis and a longitudinal axis.

As discussed above, the bed of the present invention can be used to provide rotation about longitudinal axis 38 and about a lateral axis generally perpendicular to the longitudinal axis 38. The bed can move the patient about the longitudinal axis 38 up to 360°. At the same time, Trendelenburg angles of +/−15° are also possible. For instance, a patient requiring head elevation and proning can be in reverse Trendelenburg position shown in FIG. 13 while in the supine position. As the patient 56 is rotated to the prone position, the bed also actuates the lifting apparatus or tilting apparatus to move the patient support surface to the Trendelenburg position. Therefore, when the patient is in the prone position, the patient's head will still be elevated. A graph shown in FIG. 18 illustrates rotation angles about the lateral axis and longitudinal axis 38.

Figure 19:
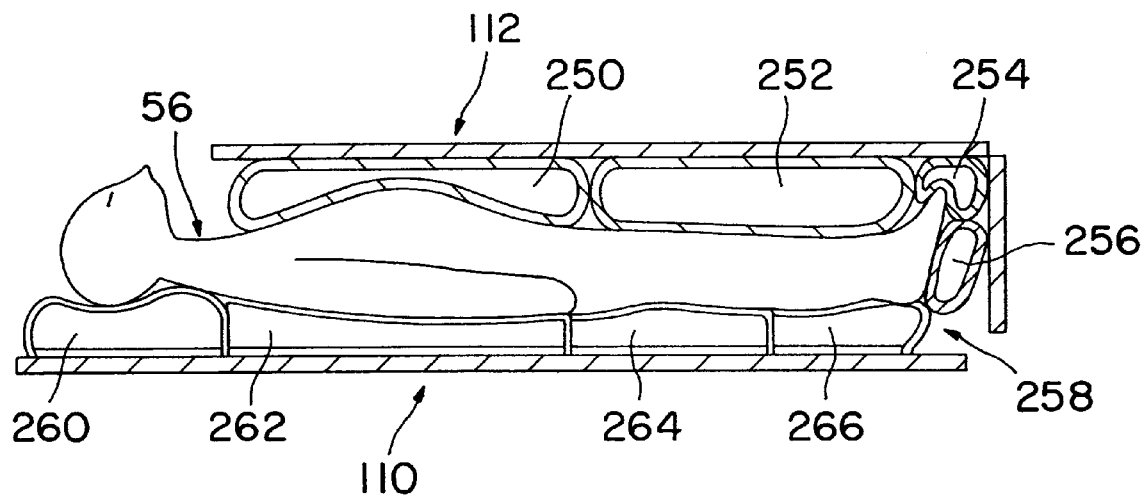
FIG. 19 is a sectional view illustrating a compression therapy apparatus of the present invention.

FIG. 19 illustrates an external chest compression device of the present invention. Illustratively, separate air cushions 250, 252, 254, 256 and 258 surround the patient 56 when the proning doors 172 and 174 are closed. The air cushions are all controlled separately. Each air cushion, 250, 252, 254, 256, and 258 may be divided into separate zones. For instance, zone 258 located below patient 56 may be divided into four separate zones 260, 262, 264 and 266 as indicated. Cushion 250 and a chest and abdomen zone 262 of lower air cushion 258 are increased in pressure to place the patient's chest cavity under varying amounts of external pressure. This may provide respiratory benefits to the patient 56, similar to prone positioning. Cushion 250 and chest and abdomen zone 262 of lower air cushion 258 may also be used to provide chest physiotherapy such as percussion or vibration therapy, either separately or together. Inflation and deflation of the cushions may also be synchronized to a patient's breathing pattern and then adjusted to wean the patient from a respirator. Cushions 252, 254, 256 and the leg and foot zones 264 and 266 of bottom cushion 258 are inflated simultaneously to provide deep vein thrombosis therapy. Inflation and deflation of all the zones is controlled by a blower coupled to a main controller of the bed 10. The controller of bed 10 can also be connected to various monitoring outputs from devices such as $SaO_2$, EKG, respiration, etc., and the pressure in the zones can be varied based upon outputs from these monitoring device outputs to synchronize treatment with the physical parameters detected. Interface pressure sensors may be included in each cushion to provide feedback to the controller.

Monitoring devices, such as a patient's blood oxygen level sensor $SaO_2$ monitoring systems are well known. The controller of the present invention is also used to control the frequency of rotation of the patient using feedback from a blood oxygen saturation monitor coupled to the patient. The processor determines whether the patient requires more or less frequent rotation based upon the blood oxygen saturation levels detected and either suggests the change in rotation frequency to the caregiver via a display or automatically adjusts the frequency of rotation of the patient support surface based on the blood oxygen saturation levels detected. The illustrated frequency is about 0.67 degrees per second. This frequency is adjusted based on the output of the blood oxygen saturation monitor.

A controller of the present invention is used to program various features of the bed to provide a sequence of treatments to the patient selected from a matrix of possible bed positions and therapies The controller can provide continuous lateral rotation of the patient about longitudinal axis 38 at different angles and frequencies. The controller may be programmed to rotate the bed further to one side than to the other during the continuous lateral rotation. In addition, the controller can be programmed to provide head elevation, for example, at selected times. The controller can be coupled to various types of sensors, such as discussed above including sensors for measuring blood oxygen level, oxygen index, end tidialed $CO_2$, etc., to adjust the treatment or position of the patient based on outputs from these sensors.

Although the invention has been described in detail with reference to a certain illustrated embodiment, variations and modifications exist within the scope and spirit of the present invention as described and defined in the following claims.

What is claimed is:

1. A bed comprising:
   a base having a first end and a second end;
   a support assembly coupled to the base adjacent the first end, the support assembly including a rotatable chive mechanism;
   a patient support assembly having a support surface for supporting a patient, the patient support assembly having a proximal end and a distal end spaced apart from the proximal end to define a longitudinal axis, the proximal end of the patient support assembly being coupled to the drive mechanism of the support assembly so that the distal end of the patient support assembly is cantilevered from the support assembly, the drive mechanism being configured to rotate the cantilevered patient support assembly at least 180° about its longitudinal axis; and
   a proning surface configured to be coupled to the patient support assembly, the proning surface being configured to support the patient in a prone position when the patient support assembly is rotated 180° about its longitudinal axis by the drive mechanism.

2. The apparatus of claim 1, wherein the support assembly includes a first support portion coupled to the base, a lifting mechanism coupled to the first support portion, and a movable frame coupled to the lifting mechanism for movement between an elevated position and a lowered position, the drive mechanism of the support assembly being coupled to the movable frame so that the patient support assembly is raised and lowered by operation of the lifting mechanism.

3. The apparatus of claim 1, wherein the support assembly is pivotably coupled to the base about a pivot axis extending transverse to the longitudinal axis of the patient support assembly.

4. The apparatus of claim 3, further comprising a pivot mechanism coupled between the base and the support assembly, the pivot mechanism being configured to rotate the support mechanism relative to the base about the pivot axis to move the support surface from a first generally horizontal position to an angled non-horizontal position.

5. The apparatus of claim 4, wherein the pivot mechanism is configured to adjust a position of the support surface relative to the base between a Trendelenburg position and a reverse Trendelenburg position.

6. The apparatus of claim 1, further comprising a lifting mechanism coupled between the base and the support assembly, the lifting mechanism being configured to move the support assembly up and down relative to the base to raise and lower the patient support assembly relative to the base.

7. A bed comprising:
a base having a first end and a second end;
a support assembly coupled to the base adjacent the first end, the support assembly including a rotatable drive mechanism, a first support portion coupled to the base, a lifting mechanism coupled to the first support portion, and a movable frame coupled to the lifting mechanism for movement between an elevated position and a lowered position, the lifting mechanism including a rodless cylinder coupled to the first support portion, the rodless cylinder including a movable carriage coupled to the movable frame; and
a patient support assembly having a support surface for supporting a patient, the patient support assembly having a proximal end and a distal end spaced apart from the proximal end to define a longitudinal axis, the proximal end of the patient support assembly being coupled to the drive mechanism of the support assembly so that the distal end of the patient support assembly is cantilevered from the support assembly, the drive mechanism being configured to rotate the cantilevered patient support assembly about its longitudinal axis, the drive mechanism of the support assembly being coupled to the movable frame so that the patient support assembly is raised and lowered by operation of the lifting mechanism.

8. The apparatus of claim 7, wherein the lifting mechanism further comprises a guide cylinder located adjacent the rodless cylinder, the guide cylinder including a guide block slidable on the guide cylinder, the guide block being coupled to the movable frame.

9. The apparatus of claim 8, wherein the lifting mechanism includes first and second rodless cylinders and first and second guide cylinders located on opposite sides of the movable frame.

10. A bed comprising:
a base having a first end and a second end,
a support assembly coupled to the base adjacent the first end, the support assembly including a rotatable drive mechanism, the drive mechanism including an annular rack rotatably coupled a front surface of the support assembly, and
a patient support assembly having a support surface for supporting a patient, the patient support assembly having a proximal end and a distal end spaced apart from the proximal end to define a longitudinal axis, the proximal end of the patient support assembly being coupled to the annular rack of the support assembly so that the distal end of the patient support assembly is cantilevered from the support assembly, the drive mechanism being configured to rotate the cantilevered patient support assembly about its longitudinal axis.

11. The apparatus of claim 10, wherein the patient support assembly includes a pair of spaced apart support arms, first ends of the patient support arms being coupled to a plate, the plate being coupled to the annular rack.

12. The apparatus of claim 11, wherein the plate is cruciform-shaped.

13. The apparatus of claim 12, wherein the first ends of the support arms extend through the cruciform-shaped plate, the first ends of the support arms being connected to a second plate spaced apart from the cruciform-shaped plate.

14. The apparatus of claim 10, further comprising a gear configured to engage the annular rack to rotate the rack relative to the front surface of the support assembly, the gear being coupled to a drive motor.

15. The apparatus of claim 10, further comprising a plurality of rotatable bearings coupled to the front surface of the support assembly to hold the annular rack on the front surface of the support assembly.

16. The apparatus of claim 10, wherein the patient support assembly includes a pair of spaced-apart support arms, the patient support surface being coupled between the support arms.

17. The apparatus of claim 16, further comprising a proning surface configured to be coupled to the support arms, the proning surface being configured to support the patient in a prone position when the patient support assembly is rotated 180° about its longitudinal ads by the drive mechanism.

18. The apparatus of claim 17, wherein the proning surface includes a head-receiving portion.

19. A bed comprising:
a base having a first end and a second end,
a support assembly coupled to the base adjacent the first end, the support assembly including a rotatable drive mechanism, the support assembly including at least one receptacle coupled to the drive mechanism, and
a patient support assembly having a support surface for supporting a patient, the patient support assembly having a proximal end and a distal end spaced apart from the proximal end to define a longitudinal axis, the proximal end of the patient support assembly being coupled to the drive mechanism of the support assembly so that the distal end of the patient support assembly is cantilevered from the support assembly, the drive mechanism being configured to rotate the cantilevered patient support assembly about its longitudinal axis, the patient support assembly being separate from the support assembly and including at least one arm configured to be selectively coupled to the at least one receptacle to permit the patient support assembly to be coupled to the support assembly with the patient on the support surface.

20. A bed comprising:
a base having a first end and a second end;
a support assembly coupled to the base adjacent the first end, the support assembly including a rotatable drive mechanism;
a patient support assembly having a support surface for supporting a patient, the patient support assembly having a proximal end and a distal end spaced apart from the proximal end to define a longitudinal axis, the proximal end of the patient support assembly being coupled to the drive mechanism of the support assembly so that the distal end of the patient support assembly is cantilevered from the support assembly, the drive mechanism being configured to rotate the cantilevered patient support assembly about its longitudinal axis; and first and second lifting mechanisms coupled to the support assembly, the patient support surface being coupled to the first and second lifting mechanisms.

21. A bed having a longitudinal axis, the bed comprising:

a base;

a frame coupled to the base;

first and second spaced apart arms coupled to the frame, the first and second arms being spaced apart from the longitudinal axis and configured to extend generally parallel to the longitudinal axis of the bed;

first and second lifting mechanisms coupled to the first and second support arms, respectively, and a patient support surface having a first side portion coupled to the first lifting mechanism and a second side portion coupled to the second lifting mechanism, the lifting mechanisms being configured to move the patient support surface up and down in a direction transverse to the first and second support arms.

22. The apparatus of claim 21, further comprising first and second movable supports coupled to the first and second arms, respectively, by the first and second lifting mechanisms, the patient support surface being coupled to the first and second movable supports.

23. The apparatus of claim 22, wherein the patient support surface includes a first portion pivotably coupled to the first movable support, a second portion pivotably coupled to the second movable support, and a locking mechanism configured to secure the first portion to the second portion.

24. The apparatus of claim 23, further comprising first and second air bladders coupled to the first and second portions of the patient support surface, respectively, to support the patient.

25. The apparatus of claim 23, further comprising a drive mechanism coupled to the frame and to the first and second arms to rotate the first and second arms about a longitudinal axis, and a proning surface including a first portion pivotably coupled to the first movable support, a second portion pivotably coupled to the second movable support, and a locking mechanism configured to secure the first portion to the second portion to form the proning surface.

26. The apparatus of claim 25, further comprising first and second air bladders coupled to the first and second portions of the proning surface, respectively, to support the patient in a prone position.

27. The apparatus of claim 21, further comprising a drive mechanism coupled to the frame and to the first and second arms to rotate the first and second arms about a longitudinal axis, and a proning surface coupled to the first and second arms.

28. The apparatus of claim 27, further comprising a controller coupled to the first and second lifting mechanisms, the controller being configured to actuate the first and second lifting mechanisms to lift the patient support surface relative to the side arms, the controller being configured to elevate the patient support surface so that a center of gravity of the patient is at or above a center axis of the first and second support arms prior to rotation of the first and second arms about the longitudinal axis.

29. The apparatus of claim 27, further comprising a plurality of cushions on the patient support surface and the proning surface to provide therapy to a patient.

30. The apparatus of claim 21, wherein the base has a first end and a second end, the frame is coupled to the base adjacent the first end, and the first and second support arms are cantilevered from the frame.

31. The apparatus of claim 21, further comprising a controller coupled to the first and second lifting mechanisms, the controller being configured to actuate the first and second lifting mechanisms in alternating directions to provide rotation of the patient support surface relative to the first and second support arms about a longitudinal axis of the patient support surface.

32. A bed comprising:

a base;

a frame coupled to the base;

first and second spaced apart arms coupled to the frame;

first and second lifting mechanisms coupled to the first and second support arms, respectively, the first and second lifting mechanisms each including first and second lifters, each lifter being separately controllable; and a patient support surface coupled to the first and second lifting mechanisms, the lifting mechanisms being configured to move the patient support surface up and down relative to the first and second support arms.

33. The apparatus of claim 32, wherein the first and second lifters each include a pair of cylinders, each cylinder including a movable piston configured to control the location of the patient support surface relative to the first and second support arms.

34. The apparatus of claim 33, wherein each pair of cylinders includes first and second cylinders pivotably coupled to the support arms and first and second pistons, respectively, pivotably coupled to the patient support surface.

35. The apparatus of claim 34, wherein the first and second pistons are pivotably coupled to the patient support surface about a single pivot axis, and the first and second cylinders pivotably are coupled to the support arms about first and second spaced apart pivot axes, respectively.

36. The apparatus of claim 32, further comprising a controller coupled to the first and second lifting mechanisms, the controller being configured to actuate the first and second lifters separately to move the patient support surface relative to the first and second arms between a Trendelenburg and a reverse Trendelenburg position.

37. The apparatus of claim 32, further comprising a drive mechanism coupled to the frame and to the first and second arms to rotate the first and second arms about a longitudinal axis, and a controller coupled to the first and second lifting mechanisms, the controller being configured to actuate the first and second lifters separately to pivot the patient support surface about an axis transverse to the first and second arms.

38. The apparatus of claim 37, wherein the controller is programmable to provide a sequence of treatments to the patient.

39. A bed comprising:

a base;

a frame coupled to the base;

first and second spaced apart arms coupled to the frame;

first and second lifting mechanisms coupled to the first and second support arms, respectively, and a patient support surface coupled to the first and second lifting mechanisms, the lifting mechanisms being configured to move the patient support surface up and down relative to the first and second support arms, the patient support surface including a fixed portion coupled to the first and second arms and a removable backboard configured to support the patient for transport to the bed from a remote location, the backboard being configured to be positioned on the fixed portion of the patient support surface while the patient is located on the backboard.

40. A bed comprising:

a base;

a frame coupled to the base;

first and second spaced apart arms coupled to the frame;

first and second lifting mechanisms coupled to the first and second support arms, respectively, a patient support surface coupled to the first and second lifting mechanisms, the lifting mechanisms being configured to move the patient support surface up and down relative to the first and second support arms; and a third lifting mechanism coupled between the base and the frame, the third lifting mechanism being configured to move the frame up and down relative to the base to raise and lower the patient support surface relative to the base.

41. A bed comprising:

a base;

a support assembly coupled to the base, the support assembly including a rotatable drive mechanism;

a patient support surface coupled to the drive mechanism of the support assembly so that the drive mechanism rotates the patient support surface about its longitudinal axis;

a monitoring device having an output signal indicating a condition of the patient; and a controller coupled to the monitoring device and the drive mechanism to control the drive mechanism to rotate the patient support surface about the longitudinal axis to a preselected angle to perform rotational therapy on the patient, the controller being configured to determine a frequency of rotation of the patient support surface in response to the output signals from the monitoring device.

42. The apparatus of claim 41, wherein the monitoring device is a blood oxygen level sensor.

43. A bed comprising:

a base;

a support assembly coupled to the base, the support assembly including a rotatable drive mechanism, a first side portion, and a second side portion; and a patient support surface configured to support a patient, the patient support surface being coupled to the support assembly, the drive mechanism being configured to rotate the patient support surface at least 180° about its longitudinal axis, the patient support surface including a first door pivotally coupled to the first side portion of the support assembly, a second door pivotally coupled to the second side portion of the support assembly, and a locking mechanism configured to secure the first door to the second door in a closed position to support the patient, the first and second doors being movable to an open position to provide access to the patient when the locking mechanism is unlocked.

44. The bed of claim 43, further comprising a proning support surface configured to support the patient in a prone position when the patient support surface is rotated 180° by the drive mechanism, the proning support surface including a third door pivotally coupled to the first side portion of the support assembly, a fourth door pivotally coupled to the second side portion of the support assembly, and a second locking mechanism configured to secure the third door to the fourth door in a closed position to support the patient in the prone position, the third and fourth doors being movable to an open position to provide access to the patient when the second locking mechanism is unlocked.

45. The apparatus of claim 44, further comprising first and second air bladders coupled to the third and fourth doors of the proning surface, respectively, to support the patient in the prone position.

46. The apparatus of claim 43, further comprising first and second air bladders coupled to the first and second doors of the patient support surface, respectively, to support the patient.

* * * * *

UNITED STATES PATENT AND TRADEMARK OFFICE
CERTIFICATE OF CORRECTION

PATENT NO.    : 6,282,736 B1
DATED         : September 4, 2001
INVENTOR(S)   : Hand et al.

It is certified that error appears in the above-identified patent and that said Letters Patent is hereby corrected as shown below:

Column 12,
Line 42, please change "chive" to -- drive --.

Signed and Sealed this

Sixth Day of July, 2004

JON W. DUDAS
*Acting Director of the United States Patent and Trademark Office*